`US007101712B1`

(12) United States Patent
Kondorosi et al.

(10) Patent No.: US 7,101,712 B1
(45) Date of Patent: Sep. 5, 2006

(54) PLANT PROTEIN WITH REPEATED WD40 MOTIFS, NUCLEIC ACID CODING FOR SAID PROTEIN, AND USES THEREOF

(75) Inventors: Eva Kondorosi, Gif sur Yvette (FR); Angel Cebolla, Séville (ES); Adam Kondorosi, Gif sur Yvette (FR)

(73) Assignee: Centre National de la Recherche Scientifique-CNRS, Paris (FR)

( * ) Notice: Subject to any disclaimer, the term of this patent is extended or adjusted under 35 U.S.C. 154(b) by 0 days.

(21) Appl. No.: 09/701,572

(22) PCT Filed: Jun. 8, 1999

(86) PCT No.: PCT/FR99/01342

§ 371 (c)(1),
(2), (4) Date: Jan. 29, 2001

(87) PCT Pub. No.: WO99/64451

PCT Pub. Date: Dec. 16, 1999

(30) Foreign Application Priority Data

Jun. 8, 1998 (FR) .................................. 98 07174

(51) Int. Cl.
*C12N 15/29* (2006.01)
*C12N 15/82* (2006.01)
*A01H 5/00* (2006.01)

(52) U.S. Cl. ................ 435/468; 435/252.3; 435/320.1; 435/419; 536/23.6; 536/24.5; 800/298

(58) Field of Classification Search ............. 435/320.1, 435/419, 468, 252.3; 536/23.6, 24.5; 800/278, 800/298
See application file for complete search history.

(56) References Cited

FOREIGN PATENT DOCUMENTS

WO  WO 95 21917  8/1995
WO  WO 98 03631  1/1998

OTHER PUBLICATIONS

GenBank Accession No. AB005230 Jul. 1997.*
Zhou et al, "COP1b, an isoform of COP1 generated by alternative splicing, has a negative effective on COP1 function in regulating light-dependent seedling development in *Arabidopsis*", 1998, Mol Gen Genet vol. 257, pp. 387-391.*
Zhou et al. COP1b, an isoform of COP1 generated by alternative splicing, has a negative effect on COP1 function in regulating light-dependent seedling development in *Arabidopsis*. Mol Gen Genet. Feb. 1998; 257 (4): 387-91.*
Broun P et al. Catalytic plasticity of fatty acid modification enzymes underlying chemical diversity of plant lipids. Science. Nov. 13, 1998;282(5392):1315-7.*
Sandler S.J. et al. Inhibition of gene expression in transformed plants by antisense RNA. Plant Molecular Biology, 1988, vol. 11 No. 3, pp. 301-310.*
van der Krol A.R. et al. Inhibition of flower pigmentation by antisense CHS genes: promoter and minimal sequence requiremen for the antisense effect. Plant Mol Biol. Apr. 1990;14(4):457-66.*
Mizukami Y. et al. Separation of AG function in floral meristem determinacy from that in reproductive organ identity by expressing antisense AG RNA. Plant Mol Biol. Aug. 1995;28(5):767-84.*
Rhoads D.M. et al. Regulation of the cyanide-resistant alternative oxidase of plant mitochondria. Identification of the cysteine residue involved in alpha-keto acid stimulation and intersubunit disulfide bond . . . J Biol Chem. Nov. 13, 1998;273(46):30750-6.*
Falcon-Perez JM et al. Functional domain analysis of the yeast ABC transporter Ycf1p by site-directed mutagenesis. J Biol Chem. Aug. 13, 1999;274(33):23584-90.*
Lamberg A. et al. Site-directed mutagenesis of the alpha subunit of human prolyl 4-hydroxylase. Identification of three histidine residues critical for catalytic activity. J Biol Chem. Apr. 28, 1995;270(17):9926-31.*
DATABASE EMBL NUCLEOTIDE AND PROTEIN SEQUENCES - Sep. 28, 1998 (Sep. 28, 1998), XP002094577 HINXTON, GB, AC = AJ224078, Brassica napus mRNA with similarity to p55cdc and fizzy genes, abstract.*
M. Luo et al., "Cloning and characterisation of a carrot cDNA coding for a WD repeat protein homologous to Drossophila fizzy, human p55CDC and yeast CDC20 proteins", Plant Molecular Biology, vol. 34, No. 2, May 1, 1997, pp. 325-330.
"Database EMBL Nucleotide and Protein Sequences", Jul. 1, 1997.
H. McKhann et al., "Cloning of a WD-repeat-containing gene from alfalfa (*Medicago sativa*): A role in hormone-mediated cell division?", Plant Molecular Biology, vol. 34, No. 5, 1997, pp. 771-780.
S.J. Sigrist et al., "Drosophila fizzy-related down-regulates mytotic cyclins and is required for cell proliferation arrest and entry into endocycles", Cell, vol. 90, 1997, pp. 671-681.
S. Yamaguchi et al., "A WD repeat protein controls the cell cycle and differentition by negatively regulating Cdc2/B-type cyclin complexes", Molecular Biology of the Cell, vol. 8, No. 12, 1997, pp. 2475-2486.
M. Schwab et al., "Yeast Hct1 is a regular of Clb2 cyclin proteolysis", Cell, vol. 90, 1997, pp. 683-693.
E. J. Neer et al., "The ancient regulatory-protein family of WD-repeat proteins", Nature, vol. 371, Sep. 22, 1994, pp. 297-300.
E. E. Patton et al., "Combinatorial control in ubiquitin-dependent proteolysis: don't Skp the F-box hypothesis", Trends in Genetics, vol. 14, No. 6, Jun. 1, 1998, pp. 236-243.
W. Hilt et al., "Proteasomes: destruction as a programme", Tibs Trends in Biochemical Sciences, vol. 21, No. 3, Mar. 1996, pp. 96-102.
C. Bai et al., "SKP1 connects cell cycle regulators to the ubiquitin proteolysis machinery through a novel motif, the F-box", Cell, vol. 86, No. 2, Jul. 26, 1996, pp. 263-274.
"Database Embl Nucleotide and Protein Sequences", Apr. 6, 1999.
A. Cebolla et al., "The mitotic Inhibitor ccs52 is required for endoreduplication and ploidy-dependent cell enlargement in plants", EMBO, vol. 18, No. 16, Aug. 1999, pp. 4476-4484.

* cited by examiner

*Primary Examiner*—Cynthia Collins
(74) *Attorney, Agent, or Firm*—Oblon, Spivak, McClelland, Maier & Neustadt, P.C.

(57) ABSTRACT

Isolated or purified nucleic acids, such as SEQ ID NO: 1, encoding a plant protein with repeated WD-40 motifs or fragments of such a protein that regulate plant differentiation or endoreplication. Vectors, host cells and plants comprising such nucleic acids, as well as antisense nucleic acids corresponding to such nucleic acids. Methods of using such nucleic acids, antisense nucleic acids, vectors, host cells, or proteins, for instance, for regulating plant differentiation or endoreplication.

28 Claims, 8 Drawing Sheets

| % Nuclei | A1 | A3 | A4 | A7 | A32 | C_b |
|---|---|---|---|---|---|---|
| 8c | 13.6 | 13.6 | 1.2 | 13.3 | 7.5 | 15.8 |
| 16c | 3.8 | 3.2 | 0 | 0.5 | 0 | 4.1 |

DNA content

PLANT PROTEIN WITH REPEATED WD40 MOTIFS, NUCLEIC ACID CODING FOR SAID PROTEIN, AND USES THEREOF

This application is a national-stage filing under 35 U.S.C. §371 of PCT/FR99/01342, filed Jun. 8, 1999. This application claims priority under 35 U.S.C. § 119 to France 98 07174, filed Jun. 8, 1998.

The invention relates to the cloning of genes involved in regulating cell division in plants, and their uses.

Most plant organs develop after germination, through differentiation from the meristems. Prior to differentiation, the cell division cycle slows down and then stops in the meristems. Simultaneously, an increase in the size of the cells, and replication of the genome not accompanied by mytosis, called "endoreplication", are frequently observed. Endoreplication is a well known phenomenon during the development of storage tissue; KOWLES [Genome, 35, pp. 68–77, (1992)] thus mention a ploidy of 6 C to 384 C during the development of the endosperm in maize.

The phenomena involved in the stoppage of cell division preceding differentiation play an essential role in plant development and ontogeny. The mechanisms involved in these phenomena are still poorly known; it appears that the inhibition of the factor for promoting the M phase, and the induction of the protein kinases of the S phase (GRAFI, Science, 269, pp. 1262–1264, (1995)] could be involved. However, no factors directly involved in this mechanism have so far been identified in plants.

BRIEF DESCRIPTION OF THE DRAWINGS

FIGS. 1B and 1C show that the CCS52Ms protein contains 7 domains with repeated WD40 motifs.

FIG. 3B shows the presence of nuclei ≧4 C.

Figure 1A:
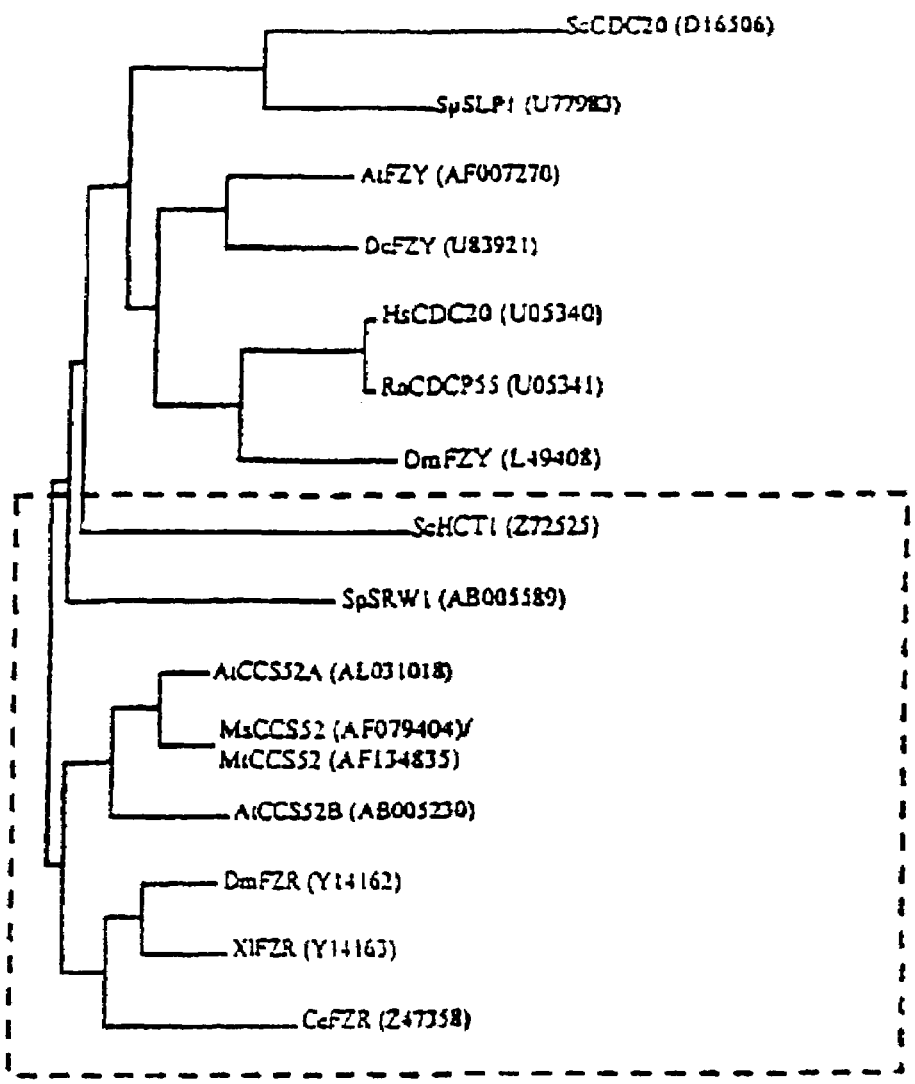
FIG. 1A represents a dendrogram of the family of proteins with repeated WD40 motifs.

The inventors undertook the study of this mechanism with the aim of discovering the means of controlling and of acting thereby on plant development and ontogenesis.

They chose, as a study model, the Rhizobium/leguminous plant symbiotic system. In this system, the Nod factors, which are lipooligosaccharide in nature and which are produced by Rhizobium, constitute mitogenic signals which locally induce the formation of a new meristem, from which the cells forming the root nodules become differentiated [TRUCHET, Nature, 351, pp. 670–673, (1991); YANG, Plant Cell, 6, pp. 1415–1426, (1994); SAVOURE, EMBO. J., 13, pp. 1093–1102, (1994)]. The nodules comprise 3 main regions: an apical region, consisting of meristematic cells; an intermediate region for invasion or for differentiation (region II), where the infection of the cells by bacteria, as well as the stoppage of cell division, accompanied by endoreplication and an increase in the size of the cells, followed by their differentiation, take place; and a region for fixation (region III), consisting of differentiated cells infected by bacteria, and where the fixation of nitrogen takes place.

During this study, the inventors isolated, from lucerne (Medicago sativa) nodules, a gene, called hereinafter ccs52, which plays an essential role in the stoppage of the cell cycle and the induction of endoreplication. Using a cDNA probe of the Medicago sativa ccs52 gene, they also isolated a homologous gene in Medicago truncatula.

The ccs52 genes of Medicago sativa (ccs52Ms), and of Medicago truncatula (ccs52Mt) encode a polypeptide of 475 amino acids having a theoretical molecular mass of 52 kDa. These polypeptides are called hereinafter CCS52Ms and CCS52Mt, respectively; the sequences of CCS52Ms and CCS52Mt differ by only 2 residues at positions 16 (R/G) and 141 (V/I).

These 2 proteins comprise repeated WD motifs, and may thus be attached to the superfamily of proteins with repeated WD motifs.

The repeated WD motifs comprise about 40 amino acids containing a number of conserved amino acids including the WD motif (Trp-Asp) which is frequently situated at one end of the repeated motif [NEER et al., Nature, 371, pp. 297–300, (1994)]. The members of this family regulate various functions, such as signal transduction, transcription, pre-mRNA splicing, organization of the cytoskeleton, vesicular fusion or the cell cycle. Although the general structure is overall similar in all the proteins, the wide functional variety of repeated WD motifs suggests that these motifs have become differentiated and have become functionally specialized. A functional homology is reflected in the number of repeated WD motifs, by a strong homology of the repeated WD motifs with equivalent positions in various proteins, compared with other repeated motifs in the same proteins, and by a significant similarity of the C- and N-terminal ends.

Comparison of the sequence of CCS52Ms with the sequences of known proteins, using the GENETICS COMPUTER GROUP GAP programme [parameters: gap weight: 1000; length weight: 0.100; average match: 0.540; average mismatch: 0.396] reveals a high homology with the proteins containing repeated WD40 motifs which are involved in the regulation of the cell cycle, and more specifically, with the Drosophila FZR proteins (57% identity), Saccharomyces cerevisiae HCT1 (46% identity), and Schizosaccharomyces pombe SRW1 (52% identity), which belong to the "fizzy-related" (FZR) family. Research carried out on databases of sequences using the BLAST programme [ALTSCHUL et al. Nucleic Acids Res. 25:3389–3402, (1997)] have also shown a strong homology of CCS52Ms with the Drosophila FZR proteins (56% identity; 70% similarity), and the Schizosaccharomyces pombe SRW1 proteins (51% identity; 67% similarity) mentioned above, as well as with the product of the X. laevis fzr gene (58% identity; 73% similarity).

The FZR proteins induce the degradation of the mitotic cyclins and are involved in the transition between cell proliferation and differentiation. It has thus been shown in Drosophila that the fzr gene is expressed at the end of cell proliferation during embryogenesis. The product of this gene causes a reduction in the mitotic cyclins, and is necessary for the stoppage of cell proliferation and the start of the endocycles [SIGRIST and LEHNER, Cell, 90, pp. 671–681, (1997)]. In *Saccharomyces cerevisiae*, HCT1 is necessary for the proteolysis of the mitotic cyclin, Clb2 [SCHWAB et al., Cell, 90, pp. 683–693, (1997)]. In *Schizosaccharomyces pombe*, the product of the swr1 gene controls the cell cycle and differentiation by negatively regulating the Cdc2/CDC13 (cyclin of the mitotic type) complexes [YAMAGUCHI et al., Mol. Biol. Cell., 8, 2475–2486, (1997)]. The FZR proteins therefore have a different role from that of the other proteins with repeated WD motifs, which are involved in cell proliferation.

In plants, no protein of the FZR family had been described prior to CCS52Ms.

The existence of a gene encoding a protein with repeated WD40 motifs and its isolation from carrot cDNA have recently been described [LUO et al., Plant Mol. Biol., 34, pp. 325–330, (1997)]. However, the product of this gene exhibits a weaker homology (44% identity and 63% similarity on the sequence comparison carried out with the BLAST programme) with the CCS52Ms protein than the FZR proteins of invertebrates and of yeast; this carrot protein is related to the cdc20, p55 and fizzy proteins, and therefore belongs to a subgroup of proteins with repeated WD40 motifs distinct from the FZR subgroup.

The search for homologues of CCS52Ms in a database of the *Arabidopsis thaliana* genome has revealed a peptide sequence deduced from a genomic clone (AB005230) and exhibiting 64% identity with CCS52Ms, which shows the existence of homologues of the ccs52Ms gene in other plants. Another peptide sequence also deduced from a genomic clone of *Arabidopsis thaliana* (AL031018, published on 17 Sep. 1998) exhibits 80% identity with CCS52Ms (44% identity and 63% similarity based on the sequence comparison carried out with the BLAST programme).

FIG. 1A represents a dendrogram of the family of proteins with repeated WD40 motifs, which shows that the CCS52 proteins form with the other FZR proteins a subfamily representing a branch which evolved separately from those respectively consisting of the CDC20, P55 and fizzy proteins.

Figure 1B:
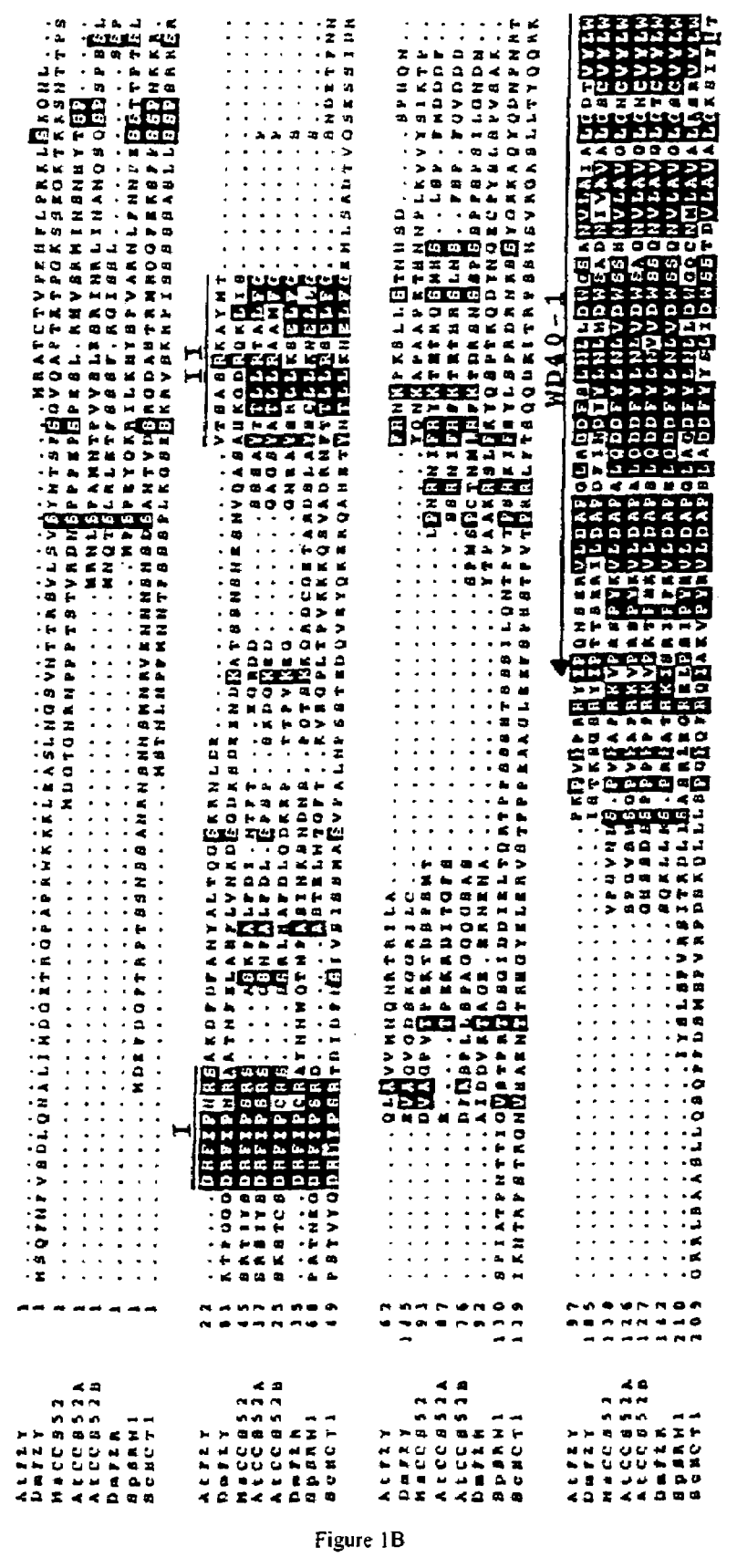
Figure 1C:
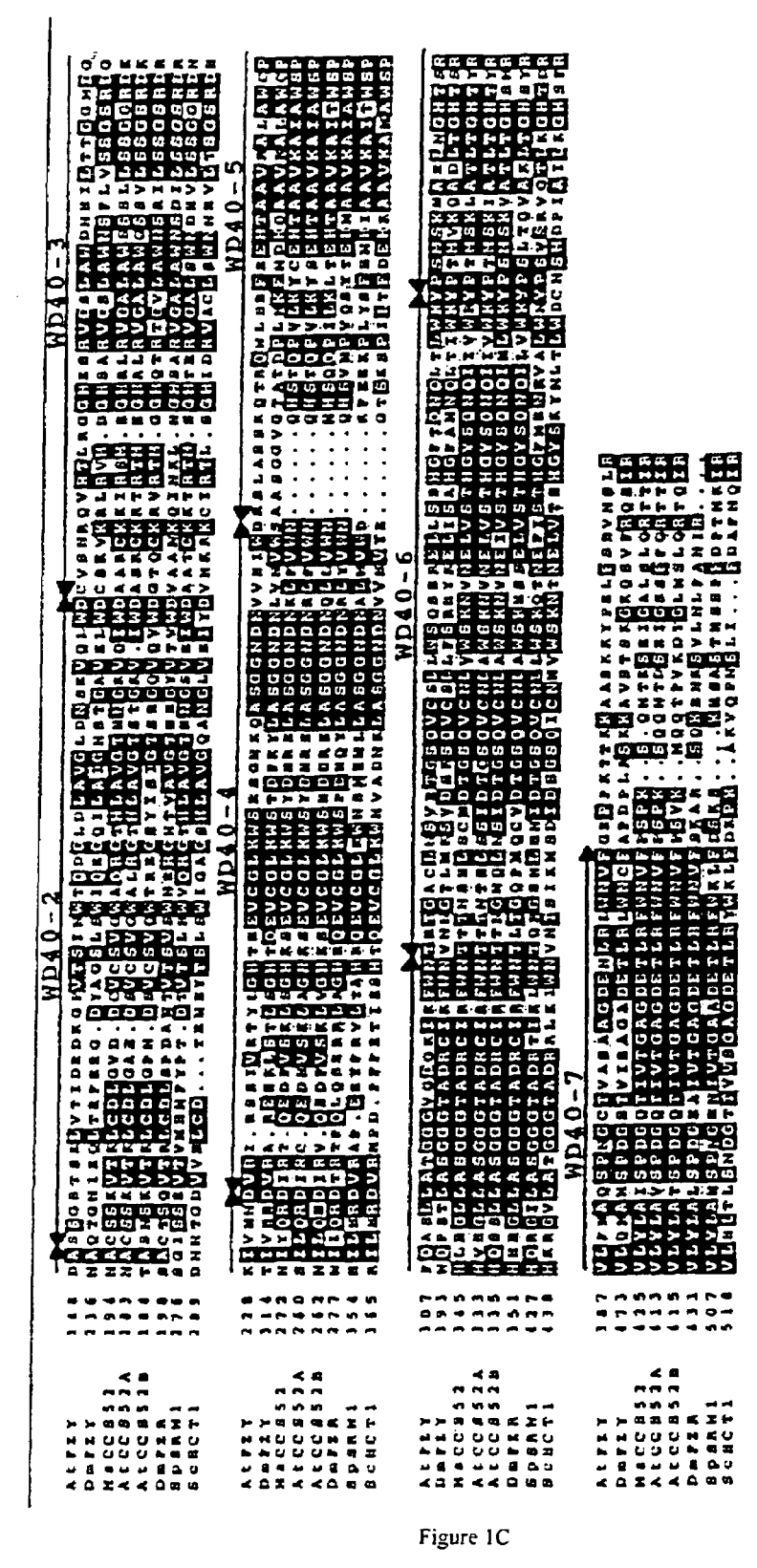

FIGS. 1B and 1C represent alignment, carried out using the "PRETTYBOX" software, of *Meedicago sativa* CCS52 (MsCCS52) sequence (SEQ IS NO:2) and the *Drosophila* FZY and FZR (DmFZY and DmFZR) sequence (SEQ ID NOS:7 and 8), of the *Saccharomyces cerevisiae* HCT1 (ScHCT1) sequence (SEQ ID NO:9), the *Schizosaccharomyces pombe* SRW1 (SpSRW1) sequence (SEQ ID NO:10), the *Arabidopsis thaliana* FZY (AtFZY) sequence (SEQ ID NO:11) and the 2 *Arabidopsis thaliana* polypeptides (AtCCS52a=peptide deduced from AL31018 (SEQ ID NO:12), and AtCCS52B=peptide deduced from AB005230 (SEQ ID NO:13).

The CCS52Ms protein contains 7 domains with repeated WD40 motifs, situated in the central and C-terminal portions of the molecule (the location of these domains numbered from I to VII, is indicated in FIGS. 1B and 1C, above the alignment of the sequences). These domains exhibit only a slight homology with each other, hence it can be concluded that they represent sites for interaction with different proteins. The latter domain (VII) comprises a potential binding site for the cyclins.

In the N-terminal portion of the CCS52Ms protein are localized a peptide sequence (DRFIPSR) which corresponds to a motif present in the FZR proteins as well as in other proteins with repeated WD40 motifs such as cdc20, p55 and fizzy, as well as a peptide sequence (AYTTLLRTALFG) which corresponds to a motif specific to the FZR family, absent from the other proteins with repeated WD40 motifs (the location of these motifs, called I and II respectively, is indicated in FIG. 1B above the alignment of the sequences).

Potential sites for phosphorylation with CDKs (cyclin-dependent kinases) are located in the N-terminal portion, at positions 43 (SPSR), 99 (TPEK), 144 (SPVK), 154 (RSP) and 155 (SPYK), as well as in the C-terminal portion at position 454 (SPK), of CCS52Ms. The sites situated at positions 43 and 144 are also present in other FZR proteins, whereas the sites situated at positions 99, 154 and 155 appear more specific to the CCS52 proteins of plants; the C-terminal site at position 454 also appears to be specific to the CCS52 proteins of plants.

A sequence of 15 amino acids RDNSPPPEPSPESLR starting at residue 16, and corresponding to a protein degradation motif PEST is also present in the N-terminal portion of CCS52Ms. This motif probably makes it possible, through the degradation of CCS52, to regulate its interactions with other proteins.

Figure 2:
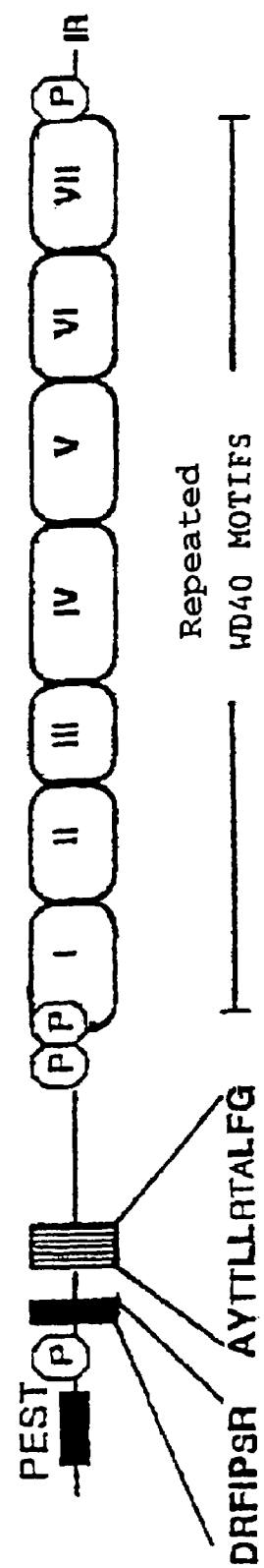
FIG. 2 schematically shows the structure of the CCS52Ms protein.

The structure of the CCS52Ms protein is schematically represented in FIG. 2, in which the position of the WD40 motifs, of the phosphorylation sites (P), of the PEST motif, and of the I and II motifs, are indicated.

The sequence of the *Medicago sativa* cDNA cloned by the inventors is represented in the sequence listing in the annexe under the number SEQ ID NO:1; the sequence of the corresponding CCS52Ms protein is represented under the number SEQ ID NO:2.

The untranslated 3' region of the transcript of this DNA comprises 2 AUUUA sequences, which correspond to sequences for instability of the mRNA, and may therefore play a role in regulating the quantity of transcripts of ccs52.

The inventors searched for the presence of homologues of ccs52Ms by Southern transfer, in diploid and tetraploid species of *Medicago*, as well as in other plants, in particular tobacco, tomato, potato, soya, wheat and rice: in all cases, several bands were detected, which indicates that ccs52 indeed represents a family of plant genes which is related to the fzr family.

The inventors studied in vivo the activity of the CCS52Ms protein and showed that it was involved in regulating cell differentiation, and in promoting endoreplication. In particular, the expression of the CCS52Ms protein in transgenic plants induces therein an increase in endoreplication and in the level of ploidy of the cells of plants. This effect could be the consequence of a blocking of mitosis by the activation of the degradation of the mitotic cyclins, which would bring about conversion of the mitotic cycles to endocycles consisting of the G1-S-G2 phases. The result of the repetition of the endocycles is the amplification of the genome and the increase in ploidy, correlated with an increase in cell volume.

The subject of the present invention is a plant protein with repeated WD40 motifs, called CCS52, characterized in that it belongs to the FZR subfamily.

According to a preferred embodiment of the present invention, the said plant protein exhibits at least 45%, and preferably at least 55% identity with the polypeptide having the sequence SEQ ID NO:2 or at least 60% and preferably at least 70% similarity with the polypeptide having the sequence SEQ ID NO:2.

The present invention includes in particular the CCS52Ms protein, its isoforms, as well as the autologous proteins of *Medicago* and the orthologous proteins of other plants, which may be attached to the family of FZR proteins.

The invention also includes proteins derived from the CCS52 proteins by addition, deletion or substitution of one or more amino acids or of one or more amino acid sequences; this may include for example proteins in which modifications have been made outside the functional regions, or alternatively proteins in which modifications have been made in order to modify their activity, for example proteins stabilized by deletion of the PEST motif.

The subject of the present invention is also a purified nucleic acid fragment, characterized in that it comprises all or part of a sequence encoding a CCS52 protein, as defined above, or its complementary sequence. In this context, the present invention includes in particular the cDNAs and the genomic DNAs of the CCS52 proteins.

Nucleic acid fragments in accordance with the present invention can be easily identified and cloned by screening plant cDNA or genomic DNA libraries with the aid of oligonucleotides derived from the ccs52Ms sequence, and in particular oligonucleotides derived from the regions of this sequence which are specific to the FZR proteins, and in particular the CCS52 proteins.

The CCS52 proteins may be produced, in particular, by expressing these nucleic acid sequences in host cells.

The subject of the present invention is also the use of a CCS52 protein, as defined above, or of a nucleic acid sequence encoding all or part of the said protein, or of its complementary sequence, for regulating the differentiation and the proliferation of plant cells.

The subject of the present invention is also the use of a protein of the FZR subfamily or of a nucleic acid sequence encoding all or part of the said protein, or of its complementary sequence, for regulating the differentiation and the proliferation of plant cells.

There may be mentioned, among such proteins, the *drosophila* FZR protein or the yeast FZR protein.

The modification of the expression and/or of the activity of CCS52 proteins in plant cells makes it possible to modify the cell cycle, by promoting either proliferation or differentiation, and to thus control the development process, in order to obtain, for example, stimulation of somatic embryogenesis, to increase in vitro regeneration of plants from calli, by increasing conversion to embryos, or to promote the development of certain organs, for example to increase the productivity of storage tissues by increasing their endoploidy.

It is possible in particular to use the cDNA sequences of CCS52 proteins or of portions of these cDNA sequences, or of their sense or antisense transcripts; this may be for example the entire sequence encoding a CCS52Ms protein, or a portion of this coding sequence, and/or all or part of the untranslated 5' and 3' regions. These sequences may be used in the sense orientation, or if it is desired to inhibit the expression of the CCS52Ms protein in a plant or in a tissue or organ thereof, in antisense orientation.

The present invention also includes recombinant DNA constructs containing at least one nucleic acid sequence in accordance with the invention.

Generally, the said nucleic acid sequence will be placed under transcriptional control of an appropriate promoter.

Advantageously, it will thus be possible to use a strong promoter in order to increase, in the host cells, the levels of expression of the CCS52 protein; this may include an inducible promoter or a constitutive promoter, a ubiquitous promoter, or a tissue-specific promoter.

The use of inducible promoters makes it possible to obtain blocking of mitosis, and the induction of endoreplication at the desired moment. The use of tissue-specific promoters makes it possible to target the action of the CCS52 protein at certain tissues and organs (for example storage tissues).

By way of examples of strong promoters which can be used in the context of the present invention, there may be mentioned: the CaMV35S [BENFLY et al., Science, 250, pp. 959–966, (1990)], the 35S promoter; the *Agrobacterium tumefaciens* T-DNA promoters: nopaline synthase, octopine synthase, mannopine synthase, 1', 2' [SANDERS et al., Nucleic Acid Res., 15, pp. 1543–1558, (1987); HOOY-KAAS and SCHILPEROORT, Plant. Mol. Biol., 19, pp. 15–38, (1992)].

By way of examples of inducible promoters which can be used in the context of the present invention, there may be mentioned: the promoter inducible by tetracycline [WEINMANN et al., Plant J., 5, pp. 559–569, (1994)]; the promoter inducible by copper [METT et al., Transgenic Res., 5, pp. 105–113, (1996)]; the promoter inducible by glucocorticoids [AOYAMA and CHUA, Plant. J., 11, pp. 605–612, (1997)].

By way of examples of tissue-specific promoters which can be used in the context of the present invention, there may be mentioned: the endosperm-specific promoter [OPSAHL-FERSTAD et al., Plant J., 12, pp. 235–246, (1997); DOAN et al., Plant Mol. Biol., 31, pp. 877–886, (1996); the nodule-specific promoters (enod12A/B or leghaemoglobin) [TRINH et al., Plant Cell Reports, (17, pp. 345–355, (1998); VIJN et al., Plant Mol. Biol., 28, pp. 1103–1110, (1995)] or early promoters inducible by the Nod factor and late promoters (promoter of cyclin D or of late nodulins (leghaemoglobin type) and promoters regulated by hormones, such as parA/B [TAKAHASHI et al., Proc. Natl. Acad. Sci, USA, 87, pp. 8013–8016, (1990)], GH3 [LIU et al., Plant Cell, 6, pp. 645–657, (1994)].

The invention includes in particular recombinant vectors carrying at least one insert containing a DNA fragment in accordance with the invention. These vectors can be used for transforming host cells.

The subject of the invention is also cells and pluricellular organisms transformed with at least one DNA sequence in accordance with the invention; this includes in particular plant cells or plants.

The present invention will be understood more clearly with the aid of the additional description which follows, and which refers to nonlimiting examples illustrating the identification, cloning and expression of the CCS52Ms gene.

EXAMPLE 1

Cloning and Sequencing of a CCS52Ms cDNA

A cDNA clone of CCS52Ms was obtained by differential screening from a cDNA library of *Medicago sativa* nodules, highly stimulated during nodular organogenesis.

The following protocol was used:

The cDNA of *M. sativa* ccs52Ms was isolated by the DD-RT-PCR (Differential Display RT-PCR) technique [LIANG and PARDEE, Science, 257, pp. 967–971, (1992)], using the RNAimage® kits (GENHUNTER CORPORATION). The RNA samples are isolated from the root region sensitive to the Nod factor of young *M. sativa* plants (growth in a nitrate-limited medium), in the absence of bacteria or inoculated with Nod$^+$ (EK1433) or Nod$^-$ (EK133) strains of *R. meliloti* for 4 days. The DD-RT-PCR ccs52Ms fragment, exhibiting an increase in the expression of the nodules, is cloned into the cloning vector PCT-TRAP (GENHUNTER CORPORATION) and used as a probe for the isolation of complete clones from a cDNA library of nodules of *M.* sativa sp. varia A2, constructed in λ-ZAP (STRATAGENE) (CRESPI et al., EMBO J., 1994, 13, 5099–5112).

Seven cDNA clones, obtained from $2.10^5$ phages, represent 2 types of cDNA differing from each other only in the 4 amino acids (16R-G, 17D-N, 33S-N, 52R-G) and the length of the 3'UTR fragment. A 99% identity for the clones, at the level of the amino acid sequence, suggests that they represent allels of the same gene in allogamous tetraploid *M. sativa*.

The sequencing of the ccs52Ms cDNA is carried out with the PERKIN-ELMER ABIprism system.

The genomic clones ccs52Ms and ccs52Mt are isolated from genomic libraries of *M. sativa* cv. Nagyszénasi and *M. trucatula* ecotype GHOR, using the ccs52Ms cDNA as hybridization probe. These genomic libraries are constructed by partial digestion of the genomic DNA with the restriction enzyme MboI and the cloning of the DNA fragments having a size of between 15 and 20 Kb into the BamHI site of λ-EMBL4.

EXAMPLE 2

Identification of the Family of the CCS52MS Gene in *Medicago* and its Expression in Various Plant Organs The existence of multiple copies of the ccs52 gene is tested for by hybridization of the Southern type in tetraploid cultivars of *M. sativa* Nagyszénasi and Cardinal and in autogamous diploid *M. truncatula*, a model plant in research on vegetables.

The plant DNA is isolated from young leaves, using the NUCLEON PHYTOPURE DNA extraction kit (AMERSHAM).

The DNA samples are digested with EcoRI and transferred onto BIOTRANS nylon membrane (+) (ICN).

The Southern hybridization is carried out in accordance with conventional protocols [(SAMBROOK, Molecular Cloning: A Laboratory Manual $2^{nd}$ edn., Cold Spring Harbor Laboratory Press, New York, (1989); AUSUBEL, Current Protocols in Molecular Biology, (1989)], under stringent conditions at 65° C. (hybridization in CG buffer; washing: 2×SSC, 0.1% SDS for twice 15 min, then 0.5×SSC, 0.1% SDS for twice 30 min).

The expression of ccs52Ms is studied by Northern analysis.

Total RNA is isolated from various organs of *M. sativa* cultivar Sitel:

from the roots, inoculated for 4 days with the *R. meliloti* Nod⁻ mutant (EK133) and with the strain overproducing Nod factors (EK1433);

from the nodules, 12, 19, 23 and 30 days after infection with *R. meliloti*, and from the stems, hypocotyls, leaves, buds, flowers, roots of plants which are 3 days old, 7 days old, roots deprived of nitrogen and which do not have root tips, roots which are 7 days old, without root tips, placed in culture in the presence of nitrate, spontaneous nodules developed in the absence of *R. meliloti*, and root tips or a culture of cells of *M. sativa* sp. varia A2.

100 mg of each of the organs tested, collected under liquid nitrogen, are used for the extraction of the RNA (RNEASY PLANT, QUIAGEN).

The RNA is loaded (10 μg per lane) onto a denaturing gel (formaldehyde) [SAMBROOK, Molecular Cloning: A Laboratory Manual $2^{nd}$ edn., Cold Spring Harbor Laboratory Press, New York, (1989)].

The DNA is transferred into a 10×SSC transfer solution [CHOMCZYNSKI et al., Analytical Biochemistry, 221, pp. 303–305, (1994)].

Both in the case of the Southern hybridization and in the case of the Northern hybridization, the ccs52Ms cDNA fragment is labelled with [α³²P]dCTP (kit MEGAPRIM, AMERSHAM). Hybridization with the Msc27 probe serves as control for the loading of the RNA (SAVOURE et al., EMBO J., 13, pp. 1093–1102, (1994)].

The results of the Southern transfer show that the probe hybridizes with various EcoRI fragments of the genomic DNA of *M. sativa* or *M. truncatula*, which indicates that ccs52Ms represents, in *Medicago*, a multigene family.

The results of the Northern transfer obtained with the total RNA of roots inoculated with the Nod⁻ EK133 mutant of *R. meliloti*, or with the EK1433 strain overproducing Nod factors and with the RNA extracted from the nodules, 12, 19, 23 and 30 days after infection with *R. meliloti* show that only a small quantity of transcripts is observed in the total RNA of the roots, which reflects the small proportion of cells involved in the organogenesis of the nodules compared with the total number of cells of the roots. By contrast, in the nodules of different ages, a high level of transcription is observed, which reflects the persistence of the apical meristems and of the regions for differentiation.

The results of the Northern transfer which are obtained with the total RNAs of: 1: culture of cells of *M. sativa* sp. varia A2, 2: stems, 3: hypocotyls, 4: leaves, 5: flower buds, 6: flowers, 7: roots of shoots which are 3 days old, 8: roots of shoots which are 7 days old, deprived of nitrogen, lacking ends, 9: root tips which are 7 days old, cultured in the presence of nitrates, lacking ends, 10: spontaneous nodules developed in the absence of *R. melioti*, 11: nitrogen-fixing nodules, 12: ends of root tips, show that the expression of ccs52Ms is not limited to the nodules, although this organ is that which contains the highest level of transcripts.

These transcripts are indeed present in variable quantities practically in all the organs, which indicates that this protein is involved in the development of each of them. Apart from the nodules, the level of transcription is also high in young shoots, and, in cell cultures, where a smaller sized mRNA is in addition detected which may correspond either to a different polyadenylation, or to the expression of a homologous copy of the gene.

Analyses were also carried out by in situ hybridization, and show that the mRNA of ccs52Ms is located mainly in the region for differentiation, and in particular at the interface between regions II and III of the nodule, which are regions where differentiation is the most active.

In parallel, expression of the G1 and mitotic type cyclins as well as of the H3 histone specific to the S phase is observed in the same regions.

This indicates that CCS52Ms is involved in the regulation of the cell cycle, probably in a manner similar to its yeast and *drosophila* homologues, that is to say by means of the proteolysis of mitotic cyclins, which inhibits mitosis and induces endoreplication cycles.

EXAMPLE 3

Expression of CCS52MS in *Schizosaccharomyces Pombe*

The expression of CCS52Ms was studied in *S. pombe* in which a functional homologue (SRW1) was recently described (YAMAGUCHI, publication cited above). The gene encoding CCS52Ms was cloned into the plasmid into pREP1 under the control of the nmt1 promoter which is repressible by thiamine.

The cDNA of ccs52Ms obtained after cleavage of λ-ZAP (STRATAGENE) is digested with AgeI and partially with EcoRV. The AgeI-EcoRV fragment of 1.6 kb representing the coding region, with the exception of the first 4 codons, is cloned into a vector SKII BLUESCRIPT (STRATAGENE) digested with XmaI (compatible with AgeI) and EcoRV. From this plasmid (pSK52B), the cDNA of ccs52Ms is cut by BamHI-EcoRV digestion and cloned into the BamHI-SmaI sites of the plasmid pREP1 [MAUNDRELL et al., Gene, 123, pp. 127–30, (1993)]. To generate an open reading frame in phase with the ATG codon for translation present in the vector under the control of the nmtI promoter, the DNA is digested with BamHI and the 5' end is completed in the presence of the Klenow enzyme and of dNTPs. The religation of the blunt ends causes correct fusion, also verified by sequencing. This plasmid, called pREP52, is used to transform competent S. pombe SP-Q01 cells and the transformants are selected on EMM-thiamine agar plates, using the ESP kit (STRATAGENE). The vectors pREP1 [MAUNDRELL et al., Gene, 123, pp. 127–30, (1993)] and pESP1 (STRATAGENE) are used as negative controls; the positive control consists of srw1 cloned into pREP1 [YAMAGUSHI et al., Mol. Biol. Cell., 8, pp. 2475–2486, (1997)].

The transformants of S. pombe SP-Q01 are cultured in 2 ml of 5 µM EMM-thiamine medium for 32 h at 30° C. The cells are washed twice with 10 ml of sterile water and resuspended in 5 ml of EMM medium. The cellular suspensions are divided into two halves: 2.5 ml are cultured with thiamine and 2.5 ml are cultured without thiamine, at 30° C. Culture aliquots are collected after 16 h and 24 h of culture and fixed with ethanol, stained with DAPI or with propidium iodide for analysis by flow cytometry and by microscopy [BEACH et al., Curr. Genet., 10, pp. 297–311, 1985)].

In the presence of thiamine, the expression of CCS52Ms is repressed and normal growth is observed.

Figure 3A:
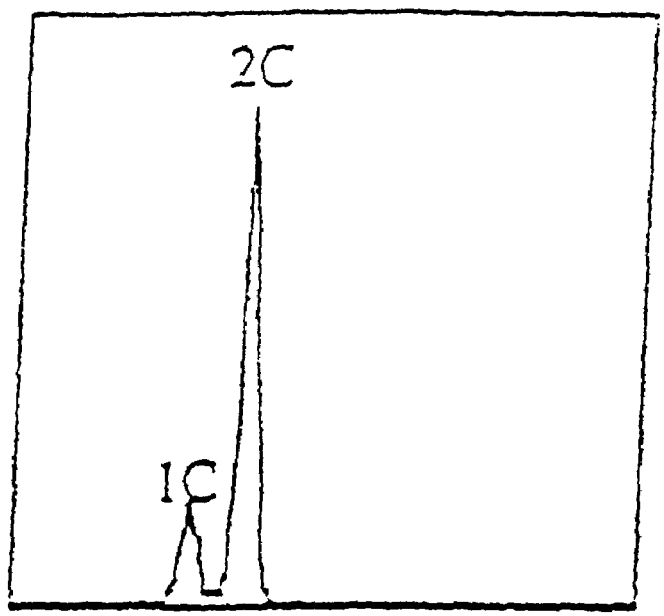
FIGS. 3A and 3B show that expression of CCS52 causes the inhibition of growth of S. pombe, which is accompanied by endoreplication (3B), but not in control cells carrying the empty vector pREP1 (3A).
Figure 3B:
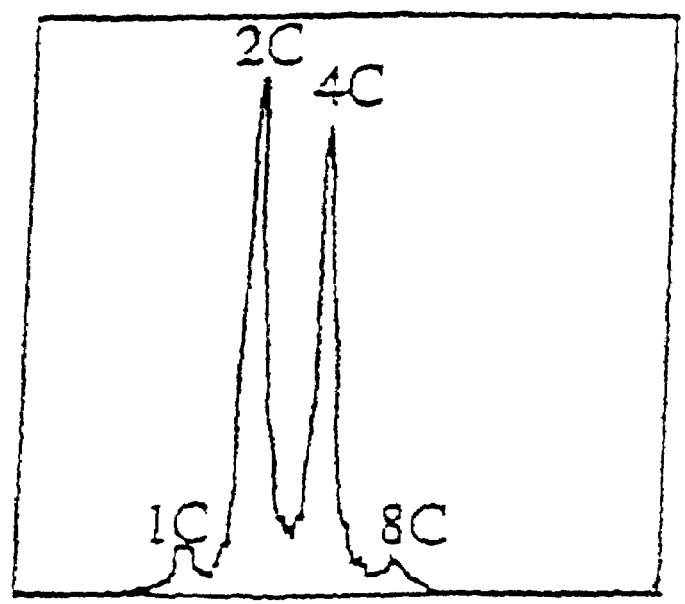

In the absence of thiamine, the expression of CCS52Ms causes the inhibition of the growth of S. pombe, which is accompanied by endoreplication as illustrated in FIG. 3B, which shows the presence of nuclei ≧4 C, which is not observed in the control cells of S. pombe, carrying the empty vector pREP1 (FIG. 3A).

The morphology of the cells is also modified by the expression of CCS52Ms. A lengthening of the cells and an increase in the size of the nuclei are observed, which are identical to those observed during the expression of SRW1 [YAMAGUSHI et al., Mol. Biol. Cell., 8, pp. 2475–2486, (1997)], whereas no morphological change is observed when S. pombe carries only the vector pREP1.

In S. pombe, SRW1 is essential for the degradation of the mitotic cyclin CDC13. To verify if CCS52 acts in the same manner, the quantity of the CDC13 was evaluated in cultures of a strain (SY1) of S. pombe, carrying a deletion in the srw1 gene, and not degrading CDC13.

The total proteins obtained from cultures of SY1 transformed with pREP1 (control) or with pREP1-ccs52 was analysed by Western transfer, and visualized with the aid of anti-CDC13 antibodies.

In parallel, the expression of CDC2 kinase and that of α-tubulin were evaluated by visualization with the aid of anti-PSTAIR and anti-α-tubulin antibodies, respectively.

The results obtained show a very high reduction in CDC13 in the cells transformed with pREP1-ccs52 compared with the control cells. By contrast, there is no variation in CDC2 and in α-tubulin.

These results confirm that CCS52 is a functional equivalent of SRW1.

EXAMPLE 4

Production of Transgenic Plants Transformed with the CCS52MS Gene

1. Expression of an Antisense Transcript and its Action on the Level of Ploidy of Medicago truncatula.

In a first instance, the level of ploidy of various organs of Medicago truncatula (plant which is naturally diploid) was determined, by flow cytometry, in nontransformed plants.

The technique used is the following:

The nuclear DNA of freshly harvested plants is analysed by flow cytometry (EPICS V, Coulter), in accordance with the method of BROWN et al., (A laboratory guide for Cellular and Molecular plant Biology, 1991, 326–345, ed. Negrutiu et al., Birkhaüser, Basel), modified such that the nuclei are stained with DAPI at a final concentration of 5 µg/ml. The nuclear buffer I is used at 1% Triton X-100 for the nodules.

In young shoots, a quantity of DNA from 2 C to 8 C is found in the root and the cotyledon, whereas the hypocotyl also contains nuclei at 16 C. In adult plants, the leaves are diploid, containing 95% of nuclei at 2 C and 5% of nuclei at 4 C. In the petioles and the nodules, nuclei from 2 C to 32 C were detected. However, the petiole contains predominantly nuclei at 2 C, whereas the nodules contain predominantly nuclei at 4 C.

An SstI-PvuII fragment of 1.2 kb containing ¾ of the coding sequence of ccs52Ms, was placed in antisense orientation under the control of the 35S promoter, in a binary vector obtained from the vector pGPTV-BAR, carrying the bar gene for resistance to the herbicide BASTA as selectable marker, and multiple cloning sites. This construct is obtained by inserting the 35S promoter into a HindIII-XbaI fragment (obtained from pBI121, CLONTECH), into the HindIII-XbaI sites of the vector pGPTV-BAR. The uidA gene is then removed from the plasmid pGPTV-BAR by XbaI-SstI digestion at the level of the multiple cloning site.

To obtain the antisense construct of ccs52Ms, the SstI-PvuII fragment of 1.2 kb is cloned into the SmaI-SstI sites of the binary vector thus obtained.

These plasmids as well as a control plasmid, containing the gus gene instead of the antisense ccs52 construct were introduced into Agrobacterium tumefaciens (EHA105) by electroporation and used to transform Medicago truncatula R108-1 according to the protocol described by HOFFMANN et al. [Mol. Plant Microbe Interaction, 10, pp. 307–315, (1997)]; TRINH ET AL. [Plant Cell Reports, 17, pp. 345–355, (1998)].

The level of ploidy of the transgenic plants obtained was analysed, as described above and the level of endogenous transcripts was evaluated by RT-PCR. To differentiate the endogenous transcripts of ccs52Mt from the antisense transcripts, the pair of primers P55CL/P55CR is used for the endogenous transcripts and the pair of primers P55BL/P55CR for the antisense transcripts.

P55BL: TTTGGGGGTTGATGATTGTG SEQ ID NO:3

P55CL: CTCTCTACCGTTCTATCTCTTGGGA SEQ ID NO:4

P5CR: GGTAAAGATGCTACTTTGGTGGTGT SEQ ID NO:5

Figure 4:
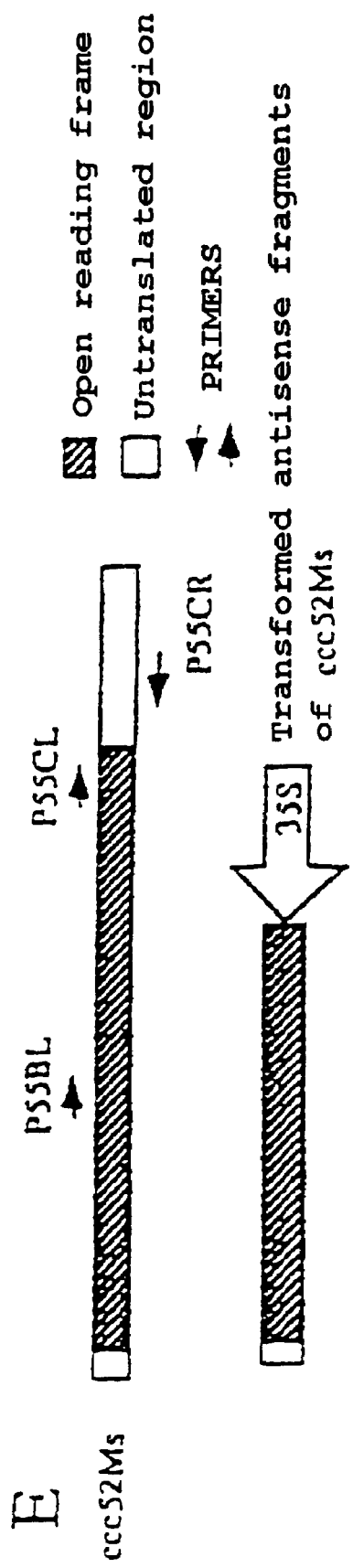
FIG. 4 shows the positions of primers P55Bl, P55CL and P55Cr.

The position of these primers is schematically represented in FIG. 4.

Figure 5A:
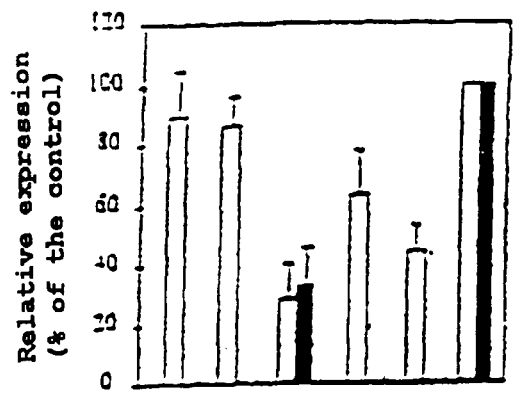
FIG. 5A shows the results of evaluation of the quantity of endogenous ccs52Mt transcripts.

FIG. 5A shows the results of evaluation of the quantity of endogenous ccs52Mt transcripts:

by RT-PCR (□) in the transgenic lines A1, A3, A4, A7 and A32 and in the control plants containing the gus gene ($C_{2n}$), and by Northern transfer (■) in A4 and $C_{2n}$ plants.

Figure 5B:
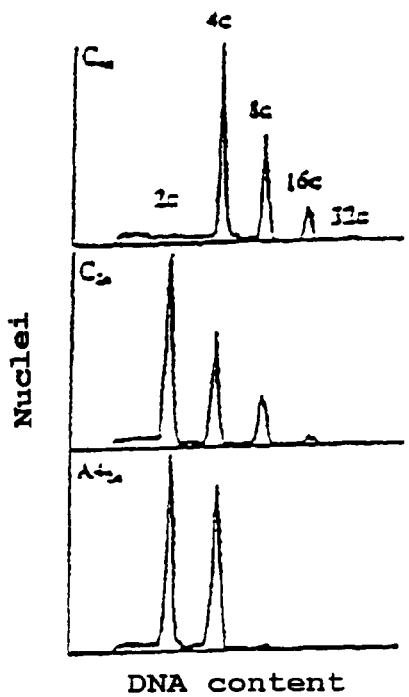
FIG. 5B shows the results of analysis by flow cytometry for petioles of control plants containing the gus gene, diploids ($C_{2n}$) or tetraploids ($C_{4n}$).

The results of analysis by flow cytometry are illustrated by FIG. 5B, for the petioles of control plants containing the gus gene, diploids ($C_{2n}$) or tetraploids ($C_{4n}$), and of plants of the A4 line.

Out of 38 regenerated transgenic plants, 3 (A4, A7 and A32) showed a significantly reduced endoploidy, and in particular the plant A4. It is also in this line that the level of expression of the endogenous transcripts of ccs52Ms is the lowest, as shown in FIG. 5B. The fact that a reduction in endoploidy was never observed before in other transgenic plants and are not observed in the control plants makes it possible to attribute this phenomenon to the impairment of the expression of CCS52Ms, and not to a secondary effect of transgenesis.

In addition, the plant A4 produces a quantity of seeds significantly less than that of the control plants. Moreover, it forms fewer side branches, and develops only 2 nodules at the level of the roots, instead of the 50 nodules on average developed by the control plants cultured under the same conditions.

The impact of the partial suppression of the expression of ccs52 on the development of the plant organs was also determined. For this purpose, the width of the petioles was measured and correlated with the percentages of endoreplicated nuclei (>4 C), in the T1 generation derived from the A4 line and in the $C_{2n}$ and $C_{4n}$ control plants.

Figure 6A:
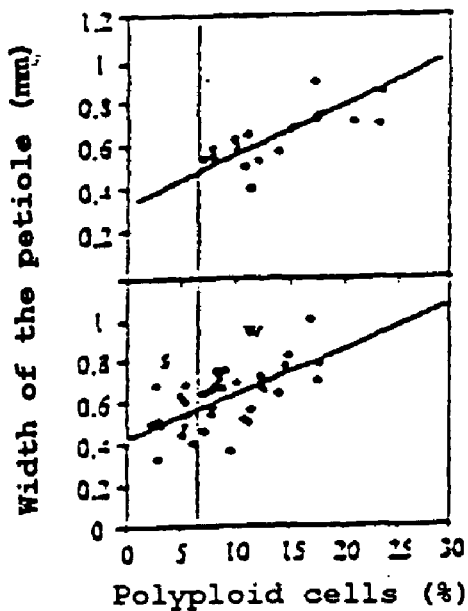
FIG. 6A shows the width of the petiole as function of the percentage of polyploid cells.

The results are illustrated in FIG. 6. FIG. 6A which represents the width of the petiole as a function of the percentage of polyploid cells shows that, in the $C_{2n}$ control plants (18 plants), the width of the petioles varies in correlation with the number of diploid cells. In the plants derived from A4 (36 plants), a more reduced variation in the size of the petioles and a lower percentage of polyploid cells are observed, which indicates that the degree of endoploidy can directly affect the final size of the plant organs.

Figure 6B:
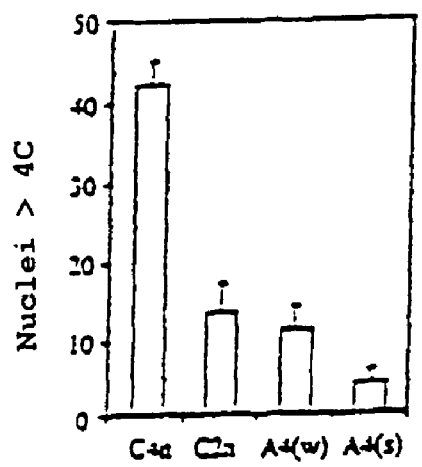
FIG. 6B shows the relative number of endoreplicated (>4 C) nuclei.

12 of the 36 T1 plants derived from A4 contain less than 6% of endoreplicated nuclei (>4 C) in their petioles (FIG. 6B). These plants [A4 (s)] were grouped together and analysed separately from the rest of the A4 T1 plants [A4(w)] which exhibit less substantial phenotypic impairments.

Figure 6C:
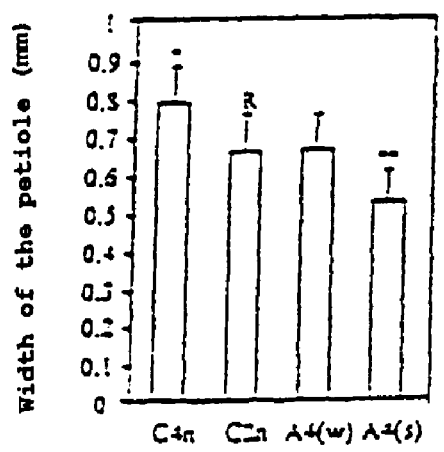
FIG. 6C shows the relative width of the petioles.

FIG. 6C shows that the width of the petioles in A4(w) plants is comparable to that of the diploid $C_{2n}$ control plants; by contrast, the width of the petioles in the A4(s) plants is significantly less than that of the diploid $C_{2n}$ control plants and the width of the petioles in the tetraploid $C_{4n}$ control plants is significantly greater than that observed in the diploid plants.

The size of the leaves (which do not contain endoreplicated cells and whose endoploidy is not therefore affected by the level of expression of CCS52) was also measured. In this case, no significant difference is observed between the A4(w) plants, the A4(s) plants and the diploid $C_{2n}$ control plants; by contrast, the size of the leaves is significantly larger in the tetraploid $C_{4n}$ control plants.

These results show that endoploidy affects the size of the plant organs, and that the modification of the expression of CCS52 acts at this level through a modification of the endoploidy.

2. Expression of the CCS52Ms Protein in Transgenic Plants.

Expression vectors containing the ccs5Ms gene under the control of the 35S promoter, as well as expression vectors containing the ccs52Ms gene, under the control of a tissue-specific promoter, were constructed according to the following protocol:

For the tissue-specific expression of CCS52Ms, the cDNA is placed under the control of the enod12AMs and Srglb3 promoters described by TRINH et al. [Plant Cell Reports, 17, pp. 345–355, (1998)], using as a vector pISV-BMCS, a derivative of pISV2301, and, instead of the complete enod12AMs promoter, only one 0.3 kb fragment thereof, considered to be sufficient for a nodule-specific expression [VIJN et al., Plant Mol. Biol., 28, pp. 1103–1110, (1995)].

Construction of pISV-BMCS: pISV2301 is digested with HindIII and SstI in order to eliminate the sequence of the 2X35S-AMV promoter, which is replaced by the following double-standed BMCS oligonucleotide:

AGCTTCCCGGGGGAGCTCTAGACTCGAGCAGCT

AGGCCCCTCGAGATCTGAGCTCG (SEQ ID NO:6).

This oligonucleotide contains the SmaI, SstI, XbaI and XhoI sites.

pISV-BMCS12A is constructed by cloning into pISV-BMCS of a fragment of the 0.3 kb of the endo12AMs promoter, obtained from the plasmid pPR89 [BAUER et al., Plant J., 10, pp. 91–105, (1996)].

pISV-BMCS-LB3 is constructed by digestion of pISV-BMCS with HindIII-SstI and cloning of a HindIII-SstI fragment containing the leghaemoglobin promoter of Sesbania rostrata from pLP32 [TRINH et al., Plant Cell Reports, 17, pp. 345–355, (1998)].

These vectors were used to transform Medicago truncatulata according to the protocol described above for the antisense sequences.

During the regeneration of the transgenic plants, a significantly greater conversion of the calli to embryos is observed in plants transformed with the constructs expressing the ccs52Ms gene, than in plants transformed with the control construct, which indicates a positive effect of CCS52Ms on somatic embryogenesis.

The invention claimed is:

1. An isolated or purified nucleic acid comprising:
   (a) a polynucleotide sequence encoding the polypeptide of SEQ ID NO: 2, or
   (b) a polynucleotide sequence encoding a polypeptide that inhibits mitosis and induces endoreplication, wherein said polynucleotide hybridizes under stringent conditions to the full-length complement of the coding portion of SEQ ID NO: 1, wherein said stringent conditions comprise at 65° C.: hybridization in CG buffer, washing in 2×SSC, 0.1% SDS for twice 15 minutes, then washing in 0.5×SSC, 0.1% SDS for twice 30 minutes.

2. An isolated or purified nucleic acid which comprises a polynucleotide sequence encoding the polypeptide of SEQ ID NO: 2.

3. The nucleic acid of claim 2 that comprises polynucleotides 182 to 1609 of SEQ ID NO: 1.

4. The nucleic acid of claim 1, which comprises a polynucleotide sequence encoding a polypeptide that inhibits mitosis and induces endoreplication, wherein said polynucleotide hybridizes under stringent conditions to the full-length complement of the coding portion of SEQ ID NO: 1, wherein said stringent conditions comprise at 65° C.: hybridization in CG buffer, washing in 2×SSC, 0.1% SDS for twice 15 minutes, then washing in 0.5×SSC, 0.1% SDS for twice 30 minutes.

5. The nucleic acid of claim 1 that is isolated from a plant.

6. A vector comprising the nucleic acid of claim 1.

7. The vector of claim 6, wherein said nucleic acid is placed under the control of a promoter.

8. The vector of claim 7, wherein said promoter is an inducible promoter, a constitutive promoter, a tissue-specific promoter or an ubiquitous promoter.

9. The vector of claim 7, wherein said promoter is an inducible promoter.

10. The vector of claim 7, wherein said promoter is a tissue specific promoter.

11. A host cell comprising the nucleic acid of claim 1.

12. A plant cell that comprises the nucleic acid of claim 1.

13. A transgenic plant comprising the nucleic acid of claim 1.

14. An isolated or purified nucleic acid comprising:
  (a) a polynucleotide sequence which comprises the full complement of the polynucleotide sequence of SEQ ID NO: 1, or
  (b) a polynucleotide sequence which comprises the full complement of the 1.2 kb SstI-PvuII fragment of SEQ ID NO: 1.

15. A vector comprising the nucleic acid of claim 14.

16. The vector of claim 15, wherein said nucleic acid is placed under the control of a promoter.

17. The vector of claim 15, wherein said promoter is an inducible promoter, a constitutive promoter, a tissue-specific promoter or an ubiquitous promoter.

18. The vector of claim 15, wherein said promoter is an inducible promoter.

19. The vector of claim 15, wherein said promoter is a tissue specific promoter.

20. A host cell comprising the nucleic acid of claim 15.

21. A plant cell that comprises the nucleic acid of claim 15.

22. A transgenic plant comprising the nucleic acid of claim 15.

23. The nucleic acid of claim 1, wherein said sequence encodes a protein comprising amino acid residues 51–55 and 57 of SEQ ID NO: 2.

24. The nucleic acid of claim 1, wherein said sequence encodes a protein comprising amino acid residues 81, 84, 85, 90 and 91 of SEQ ID NO: 2.

25. The isolated or purified nucleic acid sequence of claim 14, further comprising a promoter sequence which controls the expression of said complementary sequence.

26. A method for regulating the differentiation and the proliferation of a plant cell, comprising transforming said plant cell with the polynucleotide sequence of claim 1.

27. A method for regulating the differentiation and the proliferation of a plant cell, comprising transforming said plant cell with the polynucleotide sequence of claim 2.

28. A method for regulating the differentiation or proliferation of a plant cell, comprising transforming said plant cell with the polynucleotide sequence of claim 14.

* * * * *

SEQUENCE LISTING

<160> NUMBER OF SEQ ID NOS: 13

<210> SEQ ID NO 1
<211> LENGTH: 2006
<212> TYPE: DNA
<213> ORGANISM: Medicago sativa
<220> FEATURE:
<221> NAME/KEY: CDS
<222> LOCATION: (182)..(1609)
<223> OTHER INFORMATION:

<400> SEQUENCE: 1

```
gattcggcac gaggaagaaa caaagaaact ctctctctct atttctttct ctctgcacaa      60
ttttcgagta gtgttatttt ttaataaaaa attaattaat tttttttat ataaaagccg       120 tgcaaaaaat tcttttacag cgttcttttt tccccgggaa aaaaattaac acagctccgc     180 c atg gac gga acc ggt aat cga aat cca cca ccg act tcc acc gtc aga     229
  Met Asp Gly Thr Gly Asn Arg Asn Pro Pro Pro Thr Ser Thr Val Arg
  1               5                   10                  15 gac aat tct cca ccg cct gag cca tca ccg gag agt ctc cgt cat gta       277
Asp Asn Ser Pro Pro Pro Glu Pro Ser Pro Glu Ser Leu Arg His Val
            20                  25                  30 agc cgt atg atc aac agc aac cat tac acc tca cct tct cga aca atc       325
Ser Arg Met Ile Asn Ser Asn His Tyr Thr Ser Pro Ser Arg Thr Ile
        35                  40                  45 tac tcc gat agg ttc att ccg agt aga tct gct tcg aaa ttc gct ttg       373
Tyr Ser Asp Arg Phe Ile Pro Ser Arg Ser Ala Ser Lys Phe Ala Leu
    50                  55                  60 ttt gat atc aat act ccg aca gaa gga cgc gat gat agt tcc agc gct       421
Phe Asp Ile Asn Thr Pro Thr Glu Gly Arg Asp Asp Ser Ser Ser Ala
65                  70                  75                  80 tat acg act ctt ctg aga acg gcg ttg ttt gga ccg gat gtt gcc ggt       469
Tyr Thr Thr Leu Leu Arg Thr Ala Leu Phe Gly Pro Asp Val Ala Gly
                85                  90                  95 ccg gtt acg ccg gaa aaa acc gac tcg ccg tcg atg aca ttg ccg aat       517
Pro Val Thr Pro Glu Lys Thr Asp Ser Pro Ser Met Thr Leu Pro Asn
            100                 105                 110 agg aat att ttt agg tat aag acg gag acg aga cag tcc atg cac tcg       565
Arg Asn Ile Phe Arg Tyr Lys Thr Glu Thr Arg Gln Ser Met His Ser
        115                 120                 125 ctt tcg ccg ttt atg gat gat gat ttt gtt cct ggt gtt aat cat agt       613
Leu Ser Pro Phe Met Asp Asp Asp Phe Val Pro Gly Val Asn His Ser
    130                 135                 140 ccg gtt aag gct cct agg aag gtt cct cga tcg cct tat aag gtt ttg       661
Pro Val Lys Ala Pro Arg Lys Val Pro Arg Ser Pro Tyr Lys Val Leu
145                 150                 155                 160 gat gca cct gct ttg caa gat gat ttt tat ctg aat ctg gta gat tgg       709
Asp Ala Pro Ala Leu Gln Asp Asp Phe Tyr Leu Asn Leu Val Asp Trp
                165                 170                 175 tct tca cac aat gtg ttg gct gtt ggt ttg ggt aac tgt gtc tat ctc       757
Ser Ser His Asn Val Leu Ala Val Gly Leu Gly Asn Cys Val Tyr Leu
            180                 185                 190 tgg aat gct tgt agc agc aag gta act aaa tta tgt gat ttg ggg gtt       805
Trp Asn Ala Cys Ser Ser Lys Val Thr Lys Leu Cys Asp Leu Gly Val
        195                 200                 205 gat gat tgt gtt tgt tct gtt ggt tgg gct caa cgt ggt act cat ctt       853
Asp Asp Cys Val Cys Ser Val Gly Trp Ala Gln Arg Gly Thr His Leu
    210                 215                 220 gct gtt gga act aac aat ggt aaa gtt cag att tgg gat gca gca aga       901
Ala Val Gly Thr Asn Asn Gly Lys Val Gln Ile Trp Asp Ala Ala Arg
225                 230                 235                 240 tgc aag aag ata aga tca atg gag ggc cat cgg tta cgt gtc ggg gcc       949
Cys Lys Lys Ile Arg Ser Met Glu Gly His Arg Leu Arg Val Gly Ala
                245                 250                 255 ttg gcc tgg agt tca tct ctt ttg tct tct ggt gga cgg gat aag aat       997
Leu Ala Trp Ser Ser Ser Leu Leu Ser Ser Gly Gly Arg Asp Lys Asn
            260                 265                 270 att tat caa cga gat ata cgc aca caa gaa gat ttt gtt agt aaa ctg      1045
Ile Tyr Gln Arg Asp Ile Arg Thr Gln Glu Asp Phe Val Ser Lys Leu
```

|  |  |  |  |  |  |  |  |  |  |  |  |  |  |  |  |
|---|---|---|---|---|---|---|---|---|---|---|---|---|---|---|---|
|  | 275 |  |  |  | 280 |  |  |  |  | 285 |  |  |  |  |  |
| tca<br>Ser | gga<br>Gly<br>290 | cac<br>His | aaa<br>Lys | tca<br>Ser | gag<br>Glu<br>295 | gtt<br>Val | tgt<br>Cys | gga<br>Gly | ctg<br>Leu | aag<br>Lys<br>300 | tgg<br>Trp | tca<br>Ser | tat<br>Tyr | gat<br>Asp | aac<br>Asn | 1093 |
| cgt<br>Arg<br>305 | gag<br>Glu | ttg<br>Leu | gca<br>Ala | tct<br>Ser<br>310 | gga<br>Gly | gga<br>Gly | aat<br>Asn | gac<br>Asp | aac<br>Asn<br>315 | aaa<br>Lys | ttg<br>Leu | ttt<br>Phe | gtt<br>Val | tgg<br>Trp<br>320 | aat<br>Asn | 1141 |
| caa<br>Gln | cac<br>His | tca<br>Ser | acc<br>Thr | cag<br>Gln<br>325 | cct<br>Pro | gtc<br>Val | ctc<br>Leu | aag<br>Lys | tac<br>Tyr<br>330 | tgt<br>Cys | gag<br>Glu | cac<br>His | aca<br>Thr | gca<br>Ala<br>335 | gct<br>Ala | 1189 |
| gtt<br>Val | aaa<br>Lys | gct<br>Ala | att<br>Ile<br>340 | gca<br>Ala | tgg<br>Trp | tct<br>Ser | cct<br>Pro | cat<br>His<br>345 | ctt<br>Leu | cat<br>His | gga<br>Gly | ctt<br>Leu | ctt<br>Leu<br>350 | gca<br>Ala | tct<br>Ser | 1237 |
| gga<br>Gly | gga<br>Gly | gga<br>Gly | act<br>Thr<br>355 | gca<br>Ala | gat<br>Asp | aga<br>Arg | tgt<br>Cys | att<br>Ile<br>360 | cgt<br>Arg | ttt<br>Phe | tgg<br>Trp | aat<br>Asn | aca<br>Thr<br>365 | acc<br>Thr | aca<br>Thr | 1285 |
| aac<br>Asn | tca<br>Ser | cac<br>His<br>370 | ctt<br>Leu | agc<br>Ser | tgt<br>Cys | atg<br>Met | gac<br>Asp<br>375 | act<br>Thr | gga<br>Gly | agt<br>Ser | cag<br>Gln | gtt<br>Val<br>380 | tgc<br>Cys | aat<br>Asn | ctt<br>Leu | 1333 |
| gtc<br>Val<br>385 | tgg<br>Trp | tcc<br>Ser | aaa<br>Lys | aat<br>Asn | gtc<br>Val<br>390 | aac<br>Asn | gaa<br>Glu | cta<br>Leu | gta<br>Val | agc<br>Ser<br>395 | aca<br>Thr | cat<br>His | ggg<br>Gly | tac<br>Tyr | tcc<br>Ser<br>400 | 1381 |
| cag<br>Gln | aac<br>Asn | cag<br>Gln | att<br>Ile | att<br>Ile<br>405 | gtt<br>Val | tgg<br>Trp | aga<br>Arg | tac<br>Tyr | ccc<br>Pro<br>410 | act<br>Thr | atg<br>Met | tca<br>Ser | aag<br>Lys | ctg<br>Leu<br>415 | gcg<br>Ala | 1429 |
| act<br>Thr | ctt<br>Leu | acc<br>Thr | ggc<br>Gly<br>420 | cat<br>His | act<br>Thr | tat<br>Tyr | agg<br>Arg | gtt<br>Val<br>425 | ctc<br>Leu | tat<br>Tyr | ctt<br>Leu | gcc<br>Ala | atc<br>Ile<br>430 | tct<br>Ser | cca<br>Pro | 1477 |
| gat<br>Asp | gga<br>Gly | cag<br>Gln | act<br>Thr<br>435 | att<br>Ile | gta<br>Val | act<br>Thr | gga<br>Gly | gct<br>Ala<br>440 | gga<br>Gly | gat<br>Asp | gaa<br>Glu | acg<br>Thr | ctt<br>Leu<br>445 | agg<br>Arg | ttc<br>Phe | 1525 |
| tgg<br>Trp | aat<br>Asn | gtt<br>Val<br>450 | ttc<br>Phe | cct<br>Pro | tcc<br>Ser | cct<br>Pro | aaa<br>Lys<br>455 | tca<br>Ser | cag<br>Gln | aat<br>Asn | act<br>Thr | gaa<br>Glu<br>460 | agt<br>Ser | gaa<br>Glu | atc<br>Ile | 1573 |
| gga<br>Gly<br>465 | gca<br>Ala | tta<br>Leu | tct<br>Ser | ctt<br>Leu | gga<br>Gly<br>470 | aga<br>Arg | act<br>Thr | act<br>Thr | atc<br>Ile | agg<br>Arg<br>475 | tga | ttgatcctgg |  |  |  | 1619 | cgttgcagcc caatcatgtg gcatatttct aagtttgggt tgctgtgtag aactaaattt 1679 ctgagcggag aacaccatgg tggaaaaacc ttgaatataa aaacaccacc aaagtagcat 1739 ctttaccaac tgggagagcc ttggagggag ctataaaagt tttgatatgg ctgccggtga 1799 tattcctgca ttcatgtgta gtctcatttt atattgaaaa gatgataaca aatgggtaat 1859 ttattgtctt ggacttatac atgcattgat ggagttgtag ccaagttttt ttattactct 1919 ttttttcttt cttcttttg atagtgctct cctgcattat ttatataatt ttaagatgcg 1979 ttaacagaga aaaaaaaaa aaaaaaa 2006

<210> SEQ ID NO 2
<211> LENGTH: 475
<212> TYPE: PRT
<213> ORGANISM: Medicago sativa

<400> SEQUENCE: 2

Met Asp Gly Thr Gly Asn Arg Asn Pro Pro Thr Ser Thr Val Arg
1               5                   10                  15

Asp Asn Ser Pro Pro Glu Pro Ser Pro Glu Ser Leu Arg His Val
         20                  25                  30

Ser Arg Met Ile Asn Ser Asn His Tyr Thr Ser Pro Ser Arg Thr Ile

-continued

```
                 35                  40                  45
Tyr Ser Asp Arg Phe Ile Pro Ser Arg Ser Ala Ser Lys Phe Ala Leu
 50                  55                  60
Phe Asp Ile Asn Thr Pro Thr Glu Gly Arg Asp Asp Ser Ser Ser Ala
 65                  70                  75                  80
Tyr Thr Thr Leu Leu Arg Thr Ala Leu Phe Gly Pro Asp Val Ala Gly
                 85                  90                  95
Pro Val Thr Pro Glu Lys Thr Asp Ser Pro Ser Met Thr Leu Pro Asn
                100                 105                 110
Arg Asn Ile Phe Arg Tyr Lys Thr Glu Thr Arg Gln Ser Met His Ser
                115                 120                 125
Leu Ser Pro Phe Met Asp Asp Asp Phe Val Pro Gly Val Asn His Ser
                130                 135                 140
Pro Val Lys Ala Pro Arg Lys Val Pro Arg Ser Pro Tyr Lys Val Leu
145                 150                 155                 160
Asp Ala Pro Ala Leu Gln Asp Asp Phe Tyr Leu Asn Leu Val Asp Trp
                165                 170                 175
Ser Ser His Asn Val Leu Ala Val Gly Leu Gly Asn Cys Val Tyr Leu
                180                 185                 190
Trp Asn Ala Cys Ser Ser Lys Val Thr Lys Leu Cys Asp Leu Gly Val
                195                 200                 205
Asp Asp Cys Val Cys Ser Val Gly Trp Ala Gln Arg Gly Thr His Leu
                210                 215                 220
Ala Val Gly Thr Asn Asn Gly Lys Val Gln Ile Trp Asp Ala Ala Arg
225                 230                 235                 240
Cys Lys Lys Ile Arg Ser Met Glu Gly His Arg Leu Arg Val Gly Ala
                245                 250                 255
Leu Ala Trp Ser Ser Ser Leu Leu Ser Ser Gly Gly Arg Asp Lys Asn
                260                 265                 270
Ile Tyr Gln Arg Asp Ile Arg Thr Gln Glu Asp Phe Val Ser Lys Leu
                275                 280                 285
Ser Gly His Lys Ser Glu Val Cys Gly Leu Lys Trp Ser Tyr Asp Asn
                290                 295                 300
Arg Glu Leu Ala Ser Gly Gly Asn Asp Asn Lys Leu Phe Val Trp Asn
305                 310                 315                 320
Gln His Ser Thr Gln Pro Val Leu Lys Tyr Cys Glu His Thr Ala Ala
                325                 330                 335
Val Lys Ala Ile Ala Trp Ser Pro His Leu His Gly Leu Leu Ala Ser
                340                 345                 350
Gly Gly Gly Thr Ala Asp Arg Cys Ile Arg Phe Trp Asn Thr Thr Thr
                355                 360                 365
Asn Ser His Leu Ser Cys Met Asp Thr Gly Ser Gln Val Cys Asn Leu
                370                 375                 380
Val Trp Ser Lys Asn Val Asn Glu Leu Val Ser Thr His Gly Tyr Ser
385                 390                 395                 400
Gln Asn Gln Ile Ile Val Trp Arg Tyr Pro Thr Met Ser Lys Leu Ala
                405                 410                 415
Thr Leu Thr Gly His Thr Tyr Arg Val Leu Tyr Leu Ala Ile Ser Pro
                420                 425                 430
Asp Gly Gln Thr Ile Val Thr Gly Ala Gly Asp Glu Thr Leu Arg Phe
                435                 440                 445
Trp Asn Val Phe Pro Ser Pro Lys Ser Gln Asn Thr Glu Ser Glu Ile
450                 455                 460
```

```
Gly Ala Leu Ser Leu Gly Arg Thr Thr Ile Arg
465                 470                 475

<210> SEQ ID NO 3
<211> LENGTH: 20
<212> TYPE: DNA
<213> ORGANISM: Artificial Sequence
<220> FEATURE:
<223> OTHER INFORMATION: synthetic DNA

<400> SEQUENCE: 3
tttgggggtt gatgattgtg                                              20

<210> SEQ ID NO 4
<211> LENGTH: 25
<212> TYPE: DNA
<213> ORGANISM: Artificial Sequence
<220> FEATURE:
<223> OTHER INFORMATION: synthetic DNA

<400> SEQUENCE: 4
ctctctaccg ttctatctct tggga                                        25

<210> SEQ ID NO 5
<211> LENGTH: 25
<212> TYPE: DNA
<213> ORGANISM: Artificial Sequence
<220> FEATURE:
<223> OTHER INFORMATION: synthetic DNA

<400> SEQUENCE: 5
ggtaaagatg ctactttggt ggtgt                                        25

<210> SEQ ID NO 6
<211> LENGTH: 56
<212> TYPE: DNA
<213> ORGANISM: Artificial Sequence
<220> FEATURE:
<223> OTHER INFORMATION: synthetic DNA

<400> SEQUENCE: 6
agcttcccgg gggagctcta gactcgagca gctaggcccc tcgagatctg agctcg      56

<210> SEQ ID NO 7
<211> LENGTH: 526
<212> TYPE: PRT
<213> ORGANISM: Drosophila melanogaster

<400> SEQUENCE: 7

Met Ser Gln Phe Asn Phe Val Ser Asp Leu Gln Asn Ala Leu Ile Met
1               5                   10                  15

Asp Gly Glu Thr Arg Gly Pro Ala Pro Arg Trp Lys Lys Lys Leu Glu
                20                  25                  30

Ala Ser Leu Asn Gly Ser Val Asn Thr Thr Arg Ser Val Leu Ser Val
            35                  40                  45

Ser Tyr Asn Thr Ser Phe Ser Gly Val Gln Ala Pro Thr Lys Thr Pro
        50                  55                  60

Gly Lys Ser Ser Glu Gly Lys Thr Lys Lys Ser Asn Thr Thr Pro Ser
65                  70                  75                  80

Lys Thr Pro Gly Gly Gly Asp Arg Phe Ile Pro Asn Arg Ala Ala Thr
                85                  90                  95

Asn Phe Glu Leu Ala His Phe Leu Val Asn Lys Asp Ser Gly Asp Lys
```

-continued

```
              100                 105                 110
Ser Asp Glu Glu Asn Asp Lys Ala Thr Ser Ser Asn Ser Asn Glu Ser
            115                 120                 125
Asn Val Gln Ala Ser Ala His Lys Gly Asp Arg Gln Lys Leu Ile Ser
        130                 135                 140
Glu Val Ala Gln Val Gly Asp Ser Lys Gly Arg Ile Leu Cys Tyr
145                 150                 155                 160
Gln Asn Lys Ala Pro Ala Pro Glu Thr His Asn Asn Pro Leu Lys
                165                 170                 175
Val Val Tyr Ser Ile Lys Thr Pro Ile Ser Thr Lys Ser Gly Ser Arg
                180                 185                 190
Tyr Ile Pro Thr Thr Ser Glu Arg Ile Leu Asp Ala Pro Asp Phe Ile
            195                 200                 205
Asn Asp Tyr Tyr Leu Asn Leu Met Asp Trp Ser Ala Asp Asn Ile Val
        210                 215                 220
Ala Val Ala Leu Gly Ser Cys Val Tyr Leu Trp Asn Ala Gln Thr Gly
225                 230                 235                 240
Asn Ile Glu Gln Leu Thr Glu Phe Glu Gly Asp Tyr Ala Gly Ser
                245                 250                 255
Leu Ser Trp Ile Gln Glu Gly Gln Ile Leu Ala Ile Gly Asn Ser Thr
                260                 265                 270
Gly Ala Val Glu Leu Trp Asp Cys Ser Lys Val Lys Arg Leu Arg Val
            275                 280                 285
Met Asp Gly His Ser Ala Arg Val Gly Ser Leu Ala Trp Asn Ser Phe
        290                 295                 300
Leu Val Ser Ser Gly Ser Arg Asp Gly Thr Ile Val His His Asp Val
305                 310                 315                 320
Arg Ala Arg Glu His Lys Leu Ser Thr Leu Ser Gly His Thr Gln Glu
                325                 330                 335
Val Cys Gly Leu Lys Trp Ser Thr Asp Phe Lys Tyr Leu Ala Ser Gly
                340                 345                 350
Gly Asn Asp Asn Leu Val Asn Val Trp Ser Ala Ala Ser Gly Gly Val
            355                 360                 365
Gly Thr Ala Thr Asp Pro Leu His Lys Phe Asn Asp His Gln Ala Ala
        370                 375                 380
Val Arg Ala Leu Ala Trp Cys Pro Trp Gln Pro Ser Thr Leu Ala Ser
385                 390                 395                 400
Gly Gly Gly Thr Ala Asp Arg Cys Ile Lys Phe Trp Asn Val Asn Asn
                405                 410                 415
Gly Thr Leu Met Lys Ser Val Asp Ser Lys Ser Gln Val Cys Ser Leu
                420                 425                 430
Leu Phe Ser Arg His Tyr Lys Glu Leu Ile Ser Ala His Gly Phe Ala
            435                 440                 445
Asn Asn Gln Leu Thr Ile Trp Lys Tyr Pro Thr Met Val Lys Gln Ala
        450                 455                 460
Asp Leu Thr Gly His Thr Ser Arg Val Leu Gln Met Ala Met Ser Pro
465                 470                 475                 480
Asp Gly Ser Thr Val Ile Ser Ala Gly Ala Asp Glu Thr Leu Arg Leu
                485                 490                 495
Trp Asn Cys Phe Ala Pro Asp Pro Leu Ala Ser Lys Lys Ala Val Ser
            500                 505                 510
Thr Ser Lys Gly Lys Gln Ser Val Phe Arg Gln Ser Ile Arg
        515                 520                 525
```

<210> SEQ ID NO 8
<211> LENGTH: 478
<212> TYPE: PRT
<213> ORGANISM: Drosophila melanogaster

<400> SEQUENCE: 8

```
Met Phe Ser Pro Glu Tyr Glu Lys Arg Ile Leu Lys His Tyr Ser Pro
1               5                   10                  15

Val Ala Arg Asn Leu Phe Asn Asn Phe Glu Ser Ser Thr Thr Pro Thr
            20                  25                  30

Ser Leu Asp Arg Phe Ile Pro Cys Arg Ala Tyr Asn Asn Trp Gln Thr
        35                  40                  45

Asn Phe Ala Ser Ile Asn Lys Ser Asn Asp Asn Ser Pro Gln Thr Ser
    50                  55                  60

Lys Lys Gln Arg Asp Cys Gly Glu Thr Ala Arg Asp Ser Leu Ala Tyr
65                  70                  75                  80

Ser Cys Leu Leu Lys Asn Glu Leu Leu Gly Ser Ala Ile Asp Asp Val
                85                  90                  95

Lys Thr Ala Gly Glu Glu Arg Asn Glu Asn Ala Tyr Thr Pro Ala Ala
            100                 105                 110

Lys Arg Ser Leu Phe Lys Tyr Gln Ser Pro Thr Lys Gln Asp Tyr Asn
        115                 120                 125

Gly Glu Cys Pro Tyr Ser Leu Ser Pro Val Ser Ala Lys Ser Gln Lys
    130                 135                 140

Leu Leu Arg Ser Pro Arg Lys Ala Thr Arg Lys Ile Ser Arg Ile Pro
145                 150                 155                 160

Phe Lys Val Leu Asp Ala Pro Glu Leu Gln Asp Asp Phe Tyr Leu Asn
                165                 170                 175

Leu Val Asp Trp Ser Ser Gln Asn Val Leu Ala Val Gly Leu Gly Ser
            180                 185                 190

Cys Val Tyr Leu Trp Ser Ala Cys Thr Ser Gln Val Thr Arg Leu Cys
        195                 200                 205

Asp Leu Ser Pro Asp Ala Asn Thr Val Thr Ser Val Ser Trp Asn Glu
    210                 215                 220

Arg Gly Asn Thr Val Ala Val Gly Thr His His Gly Tyr Val Thr Val
225                 230                 235                 240

Trp Asp Val Ala Ala Asn Lys Gln Ile Asn Lys Leu Asn Gly His Ser
                245                 250                 255

Ala Arg Val Gly Ala Leu Ala Trp Asn Ser Asp Ile Leu Ser Ser Gly
            260                 265                 270

Ser Arg Asp Arg Trp Ile Ile Gln Arg Asp Thr Arg Thr Pro Gln Leu
        275                 280                 285

Gln Ser Glu Arg Arg Leu Ala Gly His Arg Gln Glu Val Cys Gly Leu
    290                 295                 300

Lys Trp Ser Pro Asp Asn Gln Tyr Leu Ala Ser Gly Gly Asn Asp Asn
305                 310                 315                 320

Arg Leu Tyr Val Trp Asn Gln His Ser Val Asn Pro Val Gln Ser Tyr
                325                 330                 335

Thr Glu His Met Ala Ala Val Lys Ala Ile Ala Trp Ser Pro His His
            340                 345                 350

His Gly Leu Leu Ala Ser Gly Gly Thr Ala Asp Arg Cys Ile Arg
        355                 360                 365

Phe Trp Asn Thr Leu Thr Gly Gln Pro Met Gln Cys Val Asp Thr Gly
```

```
            370              375              380
Ser Gln Val Cys Asn Leu Ala Trp Ser Lys His Ser Ser Glu Leu Val
385                 390                 395                 400

Ser Thr His Gly Tyr Ser Gln Asn Gln Ile Leu Val Trp Lys Tyr Pro
                405                 410                 415

Ser Leu Thr Gln Val Ala Lys Leu Thr Gly His Ser Tyr Arg Val Leu
            420                 425                 430

Tyr Leu Ala Leu Ser Pro Asp Gly Glu Ala Ile Val Thr Gly Ala Gly
            435                 440                 445

Asp Glu Thr Leu Arg Phe Trp Asn Val Phe Ser Lys Ala Arg Ser Gln
450                 455                 460

Lys Glu Asn Lys Ser Val Leu Asn Leu Phe Ala Asn Ile Arg
465                 470                 475

<210> SEQ ID NO 9
<211> LENGTH: 565
<212> TYPE: PRT
<213> ORGANISM: Saccharomyces cerevisiae

<400> SEQUENCE: 9

Met Ser Thr Asn Leu Asn Pro Phe Met Asn Thr Phe Ser Ser Ser
1               5                   10                  15

Pro Leu Lys Gly Ser Lys Ser Lys Arg Val Ser Lys His Pro Ile Ser
                20                  25                  30

Ser Ser Ser Ser Ala Ser Leu Leu Ser Ser Pro Ser Arg Arg Ser Arg
            35                  40                  45

Pro Ser Thr Val Tyr Gln Asp Arg Tyr Tyr Pro Ser Arg Thr Asp Ile
        50                  55                  60

Asp Phe Phe Ser Ile Val Ser Ile Ser Ser Met Ala Ser Val Pro Ala
65                  70                  75                  80

Leu Asn Pro Ser Ser Thr Lys Asp Gln Val Glu Tyr Gln Lys Lys Arg
                85                  90                  95

Gln Ala His Glu Thr Tyr Asn Thr Leu Leu Lys Asn Glu Leu Phe Gly
            100                 105                 110

Lys His Leu Ser Lys Asp Thr Val Gln Ser Lys Ser Ile Asp Arg
            115                 120                 125

Ile Lys Asn Thr Arg Pro Ser Thr Arg Gln Asn Val His Ala Lys Asn
        130                 135                 140

Thr Thr Arg Met Gly Tyr Glu Leu Glu Arg Val Ser Thr Phe Pro Pro
145                 150                 155                 160

Lys Ala Ala Gly Leu Lys Lys Phe Ser Pro His Ser Thr Phe Val Thr
                165                 170                 175

Pro Arg Arg Leu Phe Thr Ser Gln Gln Asp Lys Ile Thr Arg Pro Ser
            180                 185                 190

Ser Asn Ser Val Arg Gly Ala Ser Leu Leu Thr Tyr Gln Gln Arg Lys
        195                 200                 205

Gly Arg Arg Leu Ser Ala Ala Ser Leu Leu Gln Ser Gln Phe Phe Asp
210                 215                 220

Ser Met Ser Pro Val Arg Pro Asp Ser Lys Gln Leu Leu Leu Ser Pro
225                 230                 235                 240

Gly Ile Gln Phe Arg Gln Ile Ala Lys Val Pro Tyr Arg Val Leu Asp
                245                 250                 255

Ala Pro Ser Leu Ala Asp Asp Phe Tyr Tyr Ser Leu Ile Asp Trp Ser
            260                 265                 270
```

```
Ser Thr Asp Val Leu Ala Val Ala Leu Gly Lys Ser Ile Phe Leu Thr
        275                 280                 285

Asp Asn Asn Thr Gln Asp Val Glu Leu Cys Asp Thr Glu Asn Glu
        290                 295                 300

Tyr Thr Ser Leu Ser Trp Ile Gln Ala Gly Ser His Leu Ala Val Gly
305                 310                 315                 320

Gln Ala Asn Gly Leu Val Glu Ile Tyr Asp Asp Val Met Lys Arg Lys
                325                 330                 335

Cys Tyr Arg Thr Leu Ser Gly His Ile Asp Arg Val Ala Cys Leu Ser
                340                 345                 350

Trp Asn Asn His Val Leu Thr Ser Gly Ser Arg Asp His Met Ile Leu
                355                 360                 365

Met Arg Asp Val Arg Met Pro Asp Phe Phe Arg Thr Ile Lys Ser
        370                 375                 380

His Thr Gln Glu Val Cys Gly Leu Lys Trp His Val Ala Asp Asn Lys
385                 390                 395                 400

Leu Ala Ser Gly Gly Asn Asp Asn Val Val Asn Val Thr Glu Gln Thr
                405                 410                 415

Ser Lys Ser Pro Ile Leu Thr Phe Asp Glu His Lys Ala Ala Val Lys
                420                 425                 430

Ala Lys Ala Trp Ser Pro His Lys Arg Gly Val Leu Ala Thr Gly Gly
                435                 440                 445

Gly Thr Ala Asp Arg Arg Leu Lys Leu Trp Asn Val Asn Thr Ser Ile
        450                 455                 460

Lys Met Ser Asp Ile Asp Ser Gly Ser Gln Ile Cys Asn Asn Val Trp
465                 470                 475                 480

Ser Lys Asn Glu Leu Val Thr Ser His Gly Tyr Ser Lys Tyr Asn Leu
                485                 490                 495

Thr Leu Trp Asp Cys Asn Ser Met Asp Pro Ile Ala Ile Leu Lys Gly
        500                 505                 510

His Ser Phe Arg Val Leu His Leu Thr Leu Ser Asn Asp Gly Thr Thr
        515                 520                 525

Val Val Ser Gly Ala Gly Asp Glu Thr Leu Arg Tyr Trp Lys Leu Phe
530                 535                 540

Asp Lys Pro Lys Ala Lys Val Gln Pro Asn Ser Leu Lys Phe Asp Ala
545                 550                 555                 560

Phe Asn Gln Ile Arg
                565

<210> SEQ ID NO 10
<211> LENGTH: 556
<212> TYPE: PRT
<213> ORGANISM: Schizosaccharomyces pombe

<400> SEQUENCE: 10

Met Asp Glu Phe Asp Gly Phe Thr Arg Pro Thr Ser Ser Asn Ser Ser
1               5                   10                  15

Ala Asn Arg Asn Ser Asn Asn Ser Met Asn Arg Val Glu Asn Asn Asn
                20                  25                  30

Ser Asn Ser Asp Ser Ala Asn Thr Val Asp Ser Arg Gly Asp Ala His
            35                  40                  45

Thr Arg Met Arg Gln Gly Phe Glu Lys Ser Phe Pro Ser Ser Pro Asn
        50                  55                  60

Lys Lys Arg Pro Arg Thr Asn Glu Gly Asp Arg Phe Ile Pro Ser Arg
65                  70                  75                  80
```

```
Asp Ala Ser Thr Glu Leu Trp Thr Gly Phe Thr Lys Val Glu Gly Pro
                85                  90                  95

Leu Thr Pro Val Lys Lys Gln Ser Val Ala Asp Arg Asn Phe Thr
            100                 105                 110

Thr Leu Leu Arg Ser Glu Leu Phe Gly Ser Asn Asp Glu Thr Phe Asn
            115                 120                 125

Asn Ser Pro Ile Ala Thr Pro Asn Thr Thr Ile Gly Val Ser Thr Pro
        130                 135                 140

Arg Thr Asp Ser Gly Ile Asp Asp Ile Glu Leu Thr Gln Arg Thr Pro
145                 150                 155                 160

Pro Ser Ser Ser His Thr Ser Ser Ile Leu Gln Asn Thr Pro Val
                165                 170                 175

Thr Pro Ser Arg Lys Ile Phe His Tyr Leu Ser Pro Arg Asp Arg Asn
            180                 185                 190

Lys Ser Ser Tyr Gly Lys Lys Ala Gln Tyr Gln Asp Asn Pro Asn Arg
        195                 200                 205

Thr Ile Tyr Ser Leu Ser Pro Val Arg Ser Ile Thr Lys Asp Leu Ile
    210                 215                 220

Ser Ala Ser Arg Leu Glu Gly Arg Glu Leu Pro Ser Ile Pro Tyr Arg
225                 230                 235                 240

Val Leu Asp Ala Pro Gly Leu Ala Gly Asp Phe Tyr Leu Asn Leu Leu
            245                 250                 255

Asp Trp Gly Gln Cys Asn Met Leu Ala Val Ala Leu Ala Ser Arg Val
            260                 265                 270

Tyr Leu Trp Ser Gly Ile Ser Ser Glu Val Thr Val Met His Asn Phe
        275                 280                 285

Tyr Pro Thr Asp Thr Val Thr Ser Leu Arg Trp Val Gln Arg Gly Thr
    290                 295                 300

His Leu Ala Val Gly Thr His Asn Gly Ser Val Glu Ile Trp Asp Ala
305                 310                 315                 320

Ala Thr Cys Lys Lys Thr Arg Thr Met Ser Gly His Thr Glu Arg Val
            325                 330                 335

Gly Ala Leu Ser Trp Asn Asp His Val Leu Ser Ser Gly Gly Arg Asp
        340                 345                 350

Asn His Ile Leu His Arg Asp Val Arg Ala Pro Glu His Tyr Phe Arg
    355                 360                 365

Val Leu Thr Ala His Arg Gln Glu Val Cys Gly Leu Glu Trp Asn Ser
370                 375                 380

Asn Glu Asn Leu Leu Ala Ser Gly Gly Asn Asp Asn Ala Leu Met Val
385                 390                 395                 400

Trp Asp Lys Phe Glu Glu Lys Pro Leu Tyr Ser Phe His Asn His Ile
            405                 410                 415

Ala Ala Val Lys Ala Ile Thr Trp Ser Pro His Gln Arg Gly Ile Leu
            420                 425                 430

Ala Ser Gly Gly Gly Thr Ala Asp Arg Thr Ile Lys Leu Trp Asn Thr
        435                 440                 445

Gln Arg Gly Ser Met Leu His Asn Ile Asp Thr Gly Ser Gln Val Cys
    450                 455                 460

Asn Leu Leu Trp Ser Lys Gln Thr Asn Glu Phe Ile Ser Thr His Gly
465                 470                 475                 480

Phe Met Glu Asn Glu Val Ala Leu Trp Asn Tyr Pro Ser Val Ser Arg
            485                 490                 495
```

```
Val Gly Thr Leu Lys Gly His Thr Asp Arg Val Leu Tyr Leu Ala Met
            500                 505                 510

Ser Pro Asn Gly Glu Asn Ile Val Thr Gly Ala Ala Asp Glu Thr Leu
            515                 520                 525

Arg Phe Trp Lys Leu Phe Asp Ser Lys Ser Lys His Ser Ala Ser Thr
            530                 535                 540

Met Ser Ser Pro Phe Asp Pro Thr Met Lys Ile Arg
545                 550                 555

<210> SEQ ID NO 11
<211> LENGTH: 439
<212> TYPE: PRT
<213> ORGANISM: Arabidopsis thaliana

<400> SEQUENCE: 11

Met Arg Ala Thr Cys Thr Val Pro Glu His Phe Leu Pro Lys Leu Ser
1               5                   10                  15

Lys Gln Asn Leu Asp Arg Phe Ile Pro Asn Arg Ser Ala Lys Asp Phe
            20                  25                  30

Asp Phe Ala Asn Tyr Ala Leu Thr Gln Gln Ser Lys Arg Asn Leu Cys
            35                  40                  45

Lys Val Thr Ser Ala Ser Arg Lys Ala Tyr Met Thr Gln Leu Ala Val
        50                  55                  60

Val Met Asn Gln Asn Arg Thr Arg Ile Leu Ala Phe Arg Asn Lys Pro
65              70                  75                  80

Lys Ser Leu Leu Ser Thr Asn His Ser Asp Ser Pro Asn Gln Asn Pro
                85                  90                  95

Lys Pro Val Lys Pro Arg Arg Tyr Ile Pro Gln Asn Ser Lys Ala Val
            100                 105                 110

Leu Asp Ala Pro Gly Leu Ala Asp Asp Phe Ser Leu Asn Leu Leu Asp
            115                 120                 125

Trp Gln Ser Ala Asn Val Leu Ala Ile Ala Leu Gly Asp Thr Val Tyr
        130                 135                 140

Leu Trp Asp Ala Ser Ser Gly Ser Thr Ser Asp Leu Val Thr Ile Asp
145                 150                 155                 160

Lys Asp Lys Gly Pro Val Thr Ser Ile Asn Trp Thr Gln Asp Gly Leu
                165                 170                 175

Asp Leu Ala Val Gly Leu Asp Asn Ser Lys Val Gln Leu Trp Asp Cys
            180                 185                 190

Val Ser Asn Arg Gln Val Arg Thr Leu Arg Gly His Lys Ser Arg
            195                 200                 205

Val Gly Ser Leu Ala Trp Asp His His Ile Leu Thr Thr Gly His Asp
        210                 215                 220

Gly Lys Ile Val Met His Asp Val Arg Ile Arg Ser Ser Ile Val Arg
225                 230                 235                 240

Thr Tyr Leu Gly His Thr Glu Glu Val Cys Gly Leu Lys Trp Ser Trp
                245                 250                 255

Lys Ser Gly Asn Lys Gln Ala Ser Gly Gly Asn Asp Asn Val Val His
            260                 265                 270

Ile Trp Asp Ala Ser Leu Ala Ser Ser Lys Gln Thr Ala Gln Trp Leu
            275                 280                 285

His Arg Phe Arg Glu His Thr Ala Ala Val Ala Ala Leu Ala Trp Cys
        290                 295                 300

Pro Phe Gln Ala Ser Leu Leu Ala Thr Gly Gly Val Gly Asp Gln
305                 310                 315                 320
```

```
Lys Ile Lys Phe Trp Asn Thr Asn Thr Gly Ala Cys Leu Asn Ser Val
                325                 330                 335

Lys Thr Gly Ser Gln Val Cys Ser Leu Leu Trp Ser Gln Ser Glu Arg
                340                 345                 350

Glu Leu Leu Ser Ser His Gly Phe Thr Gln Asn Gln Leu Thr Leu Trp
                355                 360                 365

Lys Tyr Pro Ser Met Ser Lys Met Ala Lys Leu Asn Gly His Thr Ser
                370                 375                 380

Arg Val Leu Phe Met Ala Gln Ser Pro Asn Gly Cys Thr Val Ala Ser
385                 390                 395                 400

Ala Ala Gly Asp Glu His Leu Arg Leu Trp Asn Val Phe Gly Lys Pro
                405                 410                 415

Pro Lys Thr Thr Lys Lys Ala Ala Ser Lys Lys Tyr Pro Glu Leu Phe
                420                 425                 430

Ser Ser Val Asn Ser Leu Arg
                435

<210> SEQ ID NO 12
<211> LENGTH: 463
<212> TYPE: PRT
<213> ORGANISM: Arabidopsis thaliana

<400> SEQUENCE: 12

Met Arg Asn Leu Ser Pro Ala Met Asn Thr Pro Val Val Ser Leu Lys
1               5                   10                  15

Ser Arg Ile Asn Arg Leu Ile Asn Ala Asn Gln Gln Ser Pro Ser Pro
                20                  25                  30

Ser Ser Leu Ser Arg Ser Ile Tyr Ser Asp Arg Phe Ile Pro Ser Arg
                35                  40                  45

Ser Gly Ser Asn Phe Ala Leu Phe Asp Leu Ser Pro Ser Pro Ser Lys
                50                  55                  60

Asp Gln Lys Glu Asp Gly Ala Gly Ser Tyr Ala Thr Leu Leu Arg Ala
65                  70                  75                  80

Ala Met Phe Gly Pro Glu Thr Pro Lys Lys Ala Asp Ile Thr Gly Phe
                85                  90                  95

Ser Ser Ser Arg Asn Ile Phe Arg Phe Lys Thr Lys Thr His Arg Ser
                100                 105                 110

Leu Asn Ser Phe Ser Pro Phe Gln Val Asp Asp Ser Pro Gly Val
                115                 120                 125

Ser His Ser Gln Pro Val Phe Ala Phe Arg Lys Val Pro Arg Ser Pro
                130                 135                 140

Tyr Lys Val Leu Asp Ala Pro Ala Leu Gln Asp Asp Phe Tyr Leu Asn
145                 150                 155                 160

Leu Val Asp Trp Ser Ala Gln Asn Val Leu Ala Val Gly Leu Gly Asn
                165                 170                 175

Cys Val Tyr Leu Trp Asn Ala Cys Ser Ser Lys Val Thr Lys Leu Cys
                180                 185                 190

Asp Leu Gly Ala Arg Asp Ser Val Cys Ser Val Gly Trp Ala Leu Arg
                195                 200                 205

Gly Thr His Leu Ala Val Gly Thr Ser Thr Gly Lys Val Ile Trp Asp
                210                 215                 220

Ala Ser Arg Cys Lys Arg Thr Arg Thr Met Glu Gly His Ala Leu Arg
225                 230                 235                 240

Val Gly Ala Leu Ala Trp Gly Ser Ser Val Leu Ser Ser Gly Ser Arg
```

```
                      245                 250                 255
Asp Lys Ser Ile Leu Gln Arg Asp Ile Arg Cys Gln Glu Asp Lys Val
                260                 265                 270

Ser Lys Leu Ala Gly His Lys Ser Glu Val Cys Gly Leu Lys Trp Ser
            275                 280                 285

Tyr Asp Asn Arg Glu Leu Ala Ser Gly Gly Asn Asp Asn Ala Leu Phe
        290                 295                 300

Val Trp Asn Gln His Ser Thr Gln Pro Val Leu Lys Tyr Ser Glu His
305                 310                 315                 320

Thr Ala Ala Val Lys Ala Ile Ala Trp Ser Pro His Val His Gly Leu
                325                 330                 335

Leu Ala Ser Gly Gly Thr Ala Asp Arg Cys Ile Ala Phe Trp Asn
            340                 345                 350

Thr Thr Thr Asn Thr Asn Leu Ser Ser Ile Asp Thr Cys Ser Gln Val
        355                 360                 365

Cys Asn Leu Ala Trp Ser Lys Asn Val Asn Glu Leu Val Ser Thr His
    370                 375                 380

Gly Tyr Ser Gln Asn Gln Ile Ile Val Trp Lys Tyr Pro Thr Met Ser
385                 390                 395                 400

Lys Ile Ala Thr Leu Thr Gly His Thr Tyr Arg Val Leu Tyr Leu Ala
                405                 410                 415

Tyr Ser Pro Asp Gly Gln Thr Ile Val Thr Gly Ala Gly Asp Glu Thr
            420                 425                 430

Leu Arg Phe Trp Asn Val Phe Pro Ser Pro Lys Ser Gln Gln Asn Thr
        435                 440                 445

Asp Ser Lys Ile Gly Ser Ser Phe Phe Gly Arg Thr Thr Ile Arg
    450                 455                 460

<210> SEQ ID NO 13
<211> LENGTH: 465
<212> TYPE: PRT
<213> ORGANISM: Arabidopsis thaliana

<400> SEQUENCE: 13

Met Asn Gln Thr Ser Leu Met Leu Lys Thr Phe Ser Ser Ser Phe Arg
1               5                   10                  15

Gly Ile Ser Ser Leu Ser Ser Pro Ser Lys Ser Thr Cys Ser Asp Arg
            20                  25                  30

Phe Ile Pro Cys Arg Ser Ser Arg Leu Met Ala Phe Asp Leu Gln
        35                  40                  45

Asp Lys Lys Pro Thr Thr Pro Val Lys Arg Gly Gly Asn Arg Ala Tyr
    50                  55                  60

Ser Arg Leu Leu Lys Ser Glu Leu Phe Gly Ser Asp Phe Ala Ser Phe
65                  70                  75                  80

Leu Leu Ser Pro Ala Gly Gly Gly Ser Ala Ser Ser Pro Met Ser
                85                  90                  95

Pro Cys Thr Asn Asn Leu Arg Phe Lys Thr Asp Arg Ser Asn Ser Ser
            100                 105                 110

Pro Ser Pro Phe Ser Pro Ser Ile Leu Gly Asn Asp Asn Gly His Ser
        115                 120                 125

Ser Asp Ser Ser Pro Pro Phe Pro Pro Arg Lys Val Pro Lys Thr
    130                 135                 140

Pro Met Lys Val Leu Asp Ala Pro Ser Leu Gln Asp Asp Phe Tyr Leu
145                 150                 155                 160
```

-continued

```
Asn Val Val Asp Trp Ser Ser Gln Asn Val Leu Ala Val Gly Leu Gly
            165                 170                 175
Thr Cys Val Tyr Leu Trp Thr Ala Ser Asn Ser Lys Val Thr Lys Leu
            180                 185                 190
Cys Asp Leu Gly Pro Asn Asp Ser Val Cys Ser Val Gln Trp Thr Arg
            195                 200                 205
Glu Gly Ser Tyr Lys Ser Ile Gly Thr Ser Met Gly Gln Val Gln Val
            210                 215                 220
Trp Asp Gly Thr Gln Cys Lys Arg Val Arg Thr His Gly Gly His Gln
225                 230                 235                 240
Thr Arg Thr Gly Val Leu Ala Trp Asn Ser Arg Ile Leu Ser Ser Gly
            245                 250                 255
Ser Arg Asp Arg Asn Ile Leu Gln Asn Asp Ile Arg Val Gln Ser Asp
            260                 265                 270
Phe Val Ser Lys Leu Val Gly His Lys Ser Glu Val Cys Gly Leu Lys
            275                 280                 285
Trp Ser Met Asp Asp Arg Glu Leu Ala Ser Gly Gly Asn Asp Asn Gln
            290                 295                 300
Leu Leu Val Trp Asn Asn His Ser Gln Gln Pro Ile Leu Lys Leu Thr
305                 310                 315                 320
Glu His Thr Ala Ala Val Lys Ala Ile Thr Trp Ser Pro His Gln Ser
            325                 330                 335
Ser Leu Leu Ala Ser Gly Gly Gly Thr Ala Asp Arg Cys Ile Arg Phe
            340                 345                 350
Trp Asn Thr Thr Asn Gly Asn Gln Leu Asn Ser Ile Asp Thr Gly Ser
            355                 360                 365
Gln Val Cys Asn Leu Ala Trp Ser Lys Asn Val Asn Glu Ile Val Ser
            370                 375                 380
Thr His Gly Tyr Ser Gln Asn Gln Ile Met Leu Trp Lys Tyr Pro Ser
385                 390                 395                 400
Met Ser Lys Val Ala Thr Leu Thr Gly His Ser Met Arg Val Leu Tyr
            405                 410                 415
Leu Ala Thr Ser Pro Asp Gly Gln Thr Ile Val Thr Gly Ala Gly Asp
            420                 425                 430
Glu Thr Leu Arg Phe Trp Asn Val Phe Pro Ser Val Lys Met Gln Gln
            435                 440                 445
Thr Pro Val Lys Asp Thr Gly Leu Asn Ser Leu Gly Arg Thr Gln Ile
            450                 455                 460
Arg
465
```